US009248283B2

(12) United States Patent
Halperin et al.

(10) Patent No.: US 9,248,283 B2
(45) Date of Patent: Feb. 2, 2016

(54) BAND STOP FILTER COMPRISING AN INDUCTIVE COMPONENT DISPOSED IN A LEAD WIRE IN SERIES WITH AN ELECTRODE

(71) Applicant: Greatbatch Ltd., Clarence, NY (US)

(72) Inventors: Henry R. Halperin, Pikesville, MD (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 250 days.

(21) Appl. No.: 14/080,830

(22) Filed: Nov. 15, 2013

(65) Prior Publication Data

US 2014/0074211 A1    Mar. 13, 2014

Related U.S. Application Data

(60) Continuation of application No. 12/170,811, filed on Jul. 10, 2008, now Pat. No. 8,897,887, which is a division of application No. 11/423,073, filed on Jun. 8, 2006, now Pat. No. 8,244,370, which is a (Continued)

(51) Int. Cl.
*A61B 5/055* (2006.01)
*A61N 1/08* (2006.01)
(Continued)

(52) U.S. Cl.
CPC .............. *A61N 1/08* (2013.01); *A61B 18/1492* (2013.01); *G01R 33/287* (2013.01); *A61B 2018/00839* (2013.01); *A61B 2019/5236* (2013.01); *A61N 2001/086* (2013.01)

(58) Field of Classification Search
CPC .. A61N 1/37; A61N 1/3718; A61N 2001/086
See application file for complete search history.

(56) References Cited

U.S. PATENT DOCUMENTS 3,871,382 A    3/1975   Mann
3,968,802 A    7/1976   Ballis
(Continued)

FOREIGN PATENT DOCUMENTS

EP    0243573    11/1987
EP    0145430    5/1991
(Continued)

OTHER PUBLICATIONS

Ariel Roguin et al., Modern Pacemaker and Implantable Cardioverter/Defibrillator Systems Can Be Magnetic Resonance Imaging Safe, Circulation—Journal of the American Heart Association, Aug. 4, 2004 (originally published online Jul. 26, 2004), pp. 475-482, American Heart Association, Dallas, Texas, USA.

(Continued)

*Primary Examiner* — Christopher D Koharski
*Assistant Examiner* — Michael D Abreu
(74) *Attorney, Agent, or Firm* — Michael F. Scalise

(57) ABSTRACT

A band stop filter is provided for a lead wire of an active medical device (AMD). The band stop filter includes a capacitor in parallel with an inductor. The parallel capacitor and inductor are placed in series with the lead wire of the AMD, wherein values of capacitance and inductance are selected such that the band stop filter is resonant at a selected frequency. The Q of the inductor may be relatively maximized and the Q of the capacitor may be relatively minimized to reduce the overall Q of the band stop filter to attenuate current flow through the lead wire along a range of selected frequencies. In a preferred form, the band stop filter is integrated into a TIP and/or RING electrode for an active implantable medical device.

23 Claims, 12 Drawing Sheets

Related U.S. Application Data continuation-in-part of application No. 10/123,534, filed on Apr. 15, 2002, now Pat. No. 7,844,319.

(60) Provisional application No. 60/283,725, filed on Apr. 13, 2001.

(51) Int. Cl.
*A61B 18/14* (2006.01)
*G01R 33/28* (2006.01)
*A61B 18/00* (2006.01)
*A61B 19/00* (2006.01)

(56) References Cited

U.S. PATENT DOCUMENTS

| | | |
|---|---|---|
| 3,980,975 A | 9/1976 | Maxon, Jr. et al. |
| 4,188,598 A | 2/1980 | Hunt |
| 4,236,127 A | 11/1980 | Scherba |
| 4,295,467 A | 10/1981 | Mann et al. |
| 4,320,763 A | 3/1982 | Money |
| 4,424,551 A | 1/1984 | Stevenson et al. |
| 4,431,005 A | 2/1984 | McCormick |
| 4,437,474 A | 3/1984 | Peers-Trevarton |
| 4,445,501 A | 5/1984 | Bresler |
| 4,572,198 A | 2/1986 | Codrington |
| 4,585,001 A | 4/1986 | Belt |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,689,621 A | 8/1987 | Kleinberg |
| 4,712,555 A | 12/1987 | Thornander et al. |
| 4,746,864 A | 5/1988 | Satoh |
| 4,754,752 A | 7/1988 | Ginsburg et al. |
| 4,757,820 A | 7/1988 | Itoh |
| 4,766,381 A | 8/1988 | Conturo et al. |
| 4,788,980 A | 12/1988 | Mann et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,623 A | 8/1989 | Bradshaw et al. |
| 4,859,950 A | 8/1989 | Keren |
| 4,932,411 A | 6/1990 | Fritschy et al. |
| 4,940,052 A | 7/1990 | Mann et al. |
| 4,944,298 A | 7/1990 | Sholder |
| 4,960,106 A | 10/1990 | Kubokawa et al. |
| 4,989,608 A | 2/1991 | Ratner |
| 4,991,580 A | 2/1991 | Moore |
| 5,019,075 A | 5/1991 | Spears et al. |
| 5,044,375 A | 9/1991 | Bach, Jr. et al. |
| 5,052,404 A | 10/1991 | Hodgson |
| 5,063,348 A | 11/1991 | Kuhara et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Shturman |
| 5,197,468 A | 3/1993 | Proctor et al. |
| 5,209,233 A | 5/1993 | Holland et al. |
| 5,211,165 A | 5/1993 | Dumoulin et al. |
| 5,217,010 A | 6/1993 | Tsitlik et al. |
| 5,222,506 A | 6/1993 | Patrick et al. |
| 5,246,438 A | 9/1993 | Langberg |
| 5,251,120 A | 10/1993 | Smith |
| 5,271,400 A | 12/1993 | Dumoulin et al. |
| 5,300,108 A | 4/1994 | Rebell et al. |
| 5,306,291 A | 4/1994 | Kroll et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,333,095 A | 7/1994 | Stevenson et al. |
| 5,334,045 A | 8/1994 | Cappa et al. |
| 5,334,193 A | 8/1994 | Nardella |
| 5,348,010 A | 9/1994 | Schnall et al. |
| 5,352,979 A | 10/1994 | Conturo |
| 5,358,515 A | 10/1994 | Hurter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,404,880 A | 4/1995 | Throne |
| 5,413,104 A | 5/1995 | Buijs et al. |
| 5,419,325 A | 5/1995 | Dumoulin et al. |
| 5,428,337 A | 6/1995 | Vinciarelli et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,451,232 A | 9/1995 | Rhinehart et al. |
| 5,462,055 A | 10/1995 | Casey et al. |
| 5,466,254 A | 11/1995 | Helland |
| 5,476,095 A | 12/1995 | Schnall et al. |
| 5,476,483 A | 12/1995 | Bornzin et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,620,476 A | 4/1997 | Truex et al. |
| 5,623,241 A | 4/1997 | Minkoff |
| 5,629,622 A | 5/1997 | Scampini |
| 5,662,108 A | 9/1997 | Budd et al. |
| 5,682,897 A | 11/1997 | Pomeranz |
| 5,685,878 A | 11/1997 | Falwell et al. |
| 5,697,958 A | 12/1997 | Paul et al. |
| 5,699,801 A | 12/1997 | Atalar et al. |
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |
| 5,735,887 A | 4/1998 | Barreras et al. |
| 5,741,321 A | 4/1998 | Brennen |
| 5,751,539 A | 5/1998 | Stevenson et al. |
| 5,759,202 A | 6/1998 | Schroeppel |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,800,467 A | 9/1998 | Park et al. |
| 5,824,026 A | 10/1998 | Diaz |
| 5,824,029 A | 10/1998 | Weijand et al. |
| 5,833,608 A | 11/1998 | Acker |
| 5,836,992 A | 11/1998 | Thompson et al. |
| 5,840,031 A | 11/1998 | Crowley |
| 5,851,226 A | 12/1998 | Skubitz et al. |
| 5,864,234 A | 1/1999 | Ludeke |
| 5,868,674 A | 2/1999 | Glowinski et al. |
| 5,879,347 A | 3/1999 | Saadat |
| 5,891,134 A | 4/1999 | Goble et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,938,609 A | 8/1999 | Pomeranz |
| 5,938,692 A | 8/1999 | Rudie |
| 5,959,829 A | 9/1999 | Stevenson et al. |
| 5,964,705 A | 10/1999 | Truwit et al. |
| 5,973,906 A | 10/1999 | Stevenson et al. |
| 5,978,204 A | 11/1999 | Stevenson |
| 6,004,269 A | 12/1999 | Crowley et al. |

(56) References Cited

U.S. PATENT DOCUMENTS

| | | |
|---|---|---|
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,052,614 A | 4/2000 | Morris, Sr. et al. |
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,141,594 A | 10/2000 | Flynn et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,198,972 B1 | 3/2001 | Hartlaub et al. |
| 6,209,764 B1 | 4/2001 | Hartlaub et al. |
| 6,226,545 B1 | 5/2001 | Gilderdale |
| 6,236,205 B1 | 5/2001 | Ludeke et al. |
| 6,238,390 B1 | 5/2001 | Tu et al. |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,280,385 B1 | 8/2001 | Melzer et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,390,996 B1 | 5/2002 | Halperin et al. |
| 6,395,637 B1 | 5/2002 | Park et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,433,653 B1 | 8/2002 | Matsumura et al. |
| 6,456,481 B1 | 9/2002 | Stevenson |
| 6,459,935 B1 | 10/2002 | Piersma |
| 6,473,291 B1 | 10/2002 | Stevenson |
| 6,486,529 B2 | 11/2002 | Chi et al. |
| 6,493,591 B1 | 12/2002 | Stokes |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Molin |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,615,483 B2 | 9/2003 | Lindegren |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,675,033 B1 | 1/2004 | Lardo et al. |
| 6,675,036 B2 | 1/2004 | Kreger et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,697,675 B1 | 2/2004 | Safarevich et al. |
| 6,701,176 B1 | 3/2004 | Halperin et al. |
| 6,714,809 B2 | 3/2004 | Lee et al. |
| 6,728,575 B2 | 4/2004 | Hedberg |
| 6,728,579 B1 | 4/2004 | Lindgren et al. |
| 6,759,388 B1 | 7/2004 | Marchant et al. |
| 6,765,779 B2 | 7/2004 | Stevenson et al. |
| 6,765,780 B2 | 7/2004 | Brendel et al. |
| 6,771,067 B2 | 8/2004 | Kellman et al. |
| 6,795,730 B2 | 9/2004 | Connelly et al. |
| 6,823,215 B2 | 11/2004 | Obel et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,930,242 B1 | 8/2005 | Helfer et al. |
| 6,931,283 B1 | 8/2005 | Magnusson |
| 6,931,286 B2 | 8/2005 | Sigg et al. |
| 6,934,588 B1 | 8/2005 | Brand et al. |
| 6,944,489 B2 | 9/2005 | Zeijlemaker et al. |
| 6,944,507 B2 | 9/2005 | Froberg et al. |
| 6,949,929 B2 | 9/2005 | Gray et al. |
| 6,950,696 B2 | 9/2005 | Bjorling et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,999,818 B2 | 2/2006 | Stevenson et al. |
| 7,012,192 B2 | 3/2006 | Stevenson et al. |
| 7,013,180 B2 | 3/2006 | Villaseca et al. |
| 7,015,393 B2 | 3/2006 | Weiner et al. |
| 7,038,900 B2 | 5/2006 | Stevenson et al. |
| 7,039,455 B1 | 5/2006 | Brosovich et al. |
| 7,047,073 B2 | 5/2006 | Hoijer et al. |
| 7,050,855 B2 | 5/2006 | Zeijlemaker et al. |
| 7,091,412 B2 | 8/2006 | Wang et al. |
| 7,092,766 B1 | 8/2006 | Salys et al. |
| 7,113,387 B2 | 9/2006 | Stevenson et al. |
| 7,123,013 B2 | 10/2006 | Gray |
| 7,127,294 B1 | 10/2006 | Wang et al. |
| 7,148,783 B2 | 12/2006 | Parsche et al. |
| 7,149,578 B2 | 12/2006 | Edvardsson |
| 7,149,773 B2 | 12/2006 | Haller et al. |
| 7,155,271 B2 | 12/2006 | Halperin |
| 7,162,302 B2 | 1/2007 | Wang et al. |
| 7,164,950 B2 | 1/2007 | Kroll et al. |
| 7,174,219 B2 | 2/2007 | Wahlstrand et al. |
| 7,236,816 B2 | 6/2007 | Kumar et al. |
| 7,276,474 B2 | 10/2007 | Marchant et al. |
| 7,310,216 B2 | 12/2007 | Stevenson et al. |
| 7,319,905 B1 | 1/2008 | Morgan et al. |
| 7,363,090 B2 | 4/2008 | Halperin |
| 7,369,898 B1 | 5/2008 | Kroll et al. |
| 7,388,378 B2 | 6/2008 | Gray et al. |
| 7,422,568 B2 | 9/2008 | Yang et al. |
| 7,529,590 B2 | 5/2009 | MacDonald |
| 7,561,906 B2 | 7/2009 | Atalar et al. |
| 7,702,387 B2 | 4/2010 | Stevenson et al. |
| 7,729,770 B2 | 6/2010 | Cabelka et al. |
| 7,839,146 B2 | 11/2010 | Gray |
| 7,844,343 B2 | 11/2010 | Wahlstrand et al. |
| 7,899,551 B2 | 3/2011 | Westlund et al. |
| 8,301,249 B2 | 10/2012 | Min et al. |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0013948 A1 | 1/2003 | Russell |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144718 A1 | 7/2003 | Zeijlemaker et al. |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |

(56) References Cited

U.S. PATENT DOCUMENTS

| | | |
|---|---|---|
| 2003/0208252 A1 | 11/2003 | O'Boyle et al. |
| 2003/0212373 A1 | 11/2003 | Hall et al. |
| 2004/0015079 A1 | 1/2004 | Berger et al. |
| 2004/0034338 A1 | 2/2004 | Thierfelder et al. |
| 2004/0088012 A1 | 5/2004 | Kroll et al. |
| 2004/0167392 A1 | 8/2004 | Halperin et al. |
| 2004/0210289 A1 | 10/2004 | Wang et al. |
| 2004/0230271 A1 | 11/2004 | Wang et al. |
| 2004/0249428 A1 | 12/2004 | Wang et al. |
| 2004/0263173 A1 | 12/2004 | Gray |
| 2004/0263174 A1 | 12/2004 | Gray et al. |
| 2005/0070972 A1 | 3/2005 | Wahlstrand et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0197677 A1 | 9/2005 | Stevenson |
| 2005/0215914 A1 | 9/2005 | Bornzin et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0247472 A1 | 11/2005 | Helfer et al. |
| 2005/0248340 A1 | 11/2005 | Berkcan et al. |
| 2006/0009819 A1 | 1/2006 | Przybyszewski |
| 2006/0025820 A1 | 2/2006 | Phillips et al. |
| 2006/0030774 A1 | 2/2006 | Gray et al. |
| 2006/0041294 A1 | 2/2006 | Gray |
| 2006/0085043 A1 | 4/2006 | Stevenson |
| 2006/0100506 A1 | 5/2006 | Halperin et al. |
| 2006/0119361 A1 | 6/2006 | Karmarkar et al. |
| 2006/0200218 A1 | 9/2006 | Wahlstrand et al. |
| 2006/0211979 A1 | 9/2006 | Smith et al. |
| 2006/0229693 A1 | 10/2006 | Bauer et al. |
| 2006/0247684 A1 | 11/2006 | Halperin |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0259093 A1 | 11/2006 | Stevenson et al. |
| 2006/0271138 A1 | 11/2006 | MacDonald |
| 2007/0035910 A1 | 2/2007 | Stevenson |
| 2007/0043399 A1 | 2/2007 | Stevenson et al. |
| 2007/0083244 A1 | 4/2007 | Stevenson et al. |
| 2007/0088416 A1 | 4/2007 | Atalar et al. |
| 2007/0093142 A1 | 4/2007 | MacDonald et al. |
| 2007/0106332 A1 | 5/2007 | Denker et al. |
| 2007/0112398 A1 | 5/2007 | Stevenson |
| 2007/0123949 A1 | 5/2007 | Dabney et al. |
| 2007/0167867 A1 | 7/2007 | Wolf |
| 2007/0168005 A1 | 7/2007 | Gray |
| 2007/0168006 A1 | 7/2007 | Gray |
| 2007/0179577 A1 | 8/2007 | Marshall et al. |
| 2007/0208383 A1 | 9/2007 | Williams |
| 2007/0250143 A1 | 10/2007 | Sommer et al. |
| 2007/0255332 A1 | 11/2007 | Cabelka |
| 2007/0255377 A1 | 11/2007 | Marshall et al. |
| 2007/0288058 A1 | 12/2007 | Halperin et al. |
| 2007/0299490 A1 | 12/2007 | Yang et al. |
| 2008/0004670 A1 | 1/2008 | McVenes et al. |
| 2008/0033497 A1 | 2/2008 | Bulkes et al. |
| 2008/0039709 A1 | 2/2008 | Karmarkar |
| 2008/0049376 A1 | 2/2008 | Stevenson |
| 2008/0051854 A1 | 2/2008 | Bulkes et al. |
| 2008/0071313 A1 | 3/2008 | Stevenson |
| 2008/0116997 A1 | 5/2008 | Dabney |
| 2008/0132986 A1 | 6/2008 | Gray et al. |
| 2008/0132987 A1 | 6/2008 | Westlund |
| 2008/0161886 A1 | 7/2008 | Stevenson et al. |
| 2008/0195186 A1 | 8/2008 | Li et al. |
| 2008/0195187 A1 | 8/2008 | Li et al. |
| 2008/0221638 A1 | 9/2008 | Wedan et al. |
| 2008/0243218 A1 | 10/2008 | Bottomley et al. |
| 2008/0262584 A1 | 10/2008 | Bottomley et al. |
| 2008/0262592 A1 | 10/2008 | Jordan et al. |
| 2008/0269591 A1 | 10/2008 | Halperin et al. |
| 2009/0099440 A1 | 4/2009 | Vohl |
| 2009/0099555 A1 | 4/2009 | Vohl et al. |
| 2009/0163980 A1 | 6/2009 | Stevenson |
| 2009/0243756 A1 | 10/2009 | Stevenson et al. |
| 2009/0281592 A1 | 11/2009 | Vase |
| 2010/0010602 A1 | 1/2010 | Wedan et al. |
| 2010/0016936 A1 | 1/2010 | Stevenson et al. |
| 2010/0023095 A1 | 1/2010 | Stevenson et al. |
| 2010/0076538 A1 | 3/2010 | Desai et al. |
| 2010/0114276 A1 | 5/2010 | Min et al. |
| 2010/0114277 A1 | 5/2010 | Zhao et al. |
| 2010/0138192 A1 | 6/2010 | Min |
| 2010/0160989 A1 | 6/2010 | Legay |
| 2010/0174348 A1 | 7/2010 | Bulkes et al. |
| 2010/0174349 A1 | 7/2010 | Stevenson et al. |
| 2010/0217264 A1 | 8/2010 | Odom et al. |
| 2010/0217341 A1 | 8/2010 | John et al. |
| 2010/0234907 A1 | 9/2010 | Dobak, III |
| 2011/0043297 A1 | 2/2011 | Stevenson et al. |

FOREIGN PATENT DOCUMENTS

| | | |
|---|---|---|
| EP | 466424 | 1/1992 |
| EP | 557127 | 8/1993 |
| EP | 0673621 | 9/1995 |
| EP | 0498996 | 3/1997 |
| EP | 0930509 | 12/1998 |
| EP | 1021730 | 4/1999 |
| EP | 1469910 | 12/2006 |
| EP | 2025361 | 11/2007 |
| EP | 1883449 | 1/2009 |
| JP | 60141034 | 7/1985 |
| JP | 61181925 | 8/1985 |
| JP | 62233905 | 10/1987 |
| JP | 4071536 | 3/1992 |
| JP | 6054823 | 3/1994 |
| JP | 6199470902 | 3/1994 |
| JP | 994238 | 4/1997 |
| JP | 11239572 | 9/1999 |
| WO | 87/04080 | 7/1987 |
| WO | 92/10213 | 6/1992 |
| WO | 94/23782 | 10/1994 |
| WO | 97/40396 | 10/1997 |
| WO | 98/52461 | 11/1998 |
| WO | 99/19739 | 4/1999 |
| WO | 00/10456 | 3/2000 |
| WO | 00/25672 | 5/2000 |
| WO | 02/083016 | 10/2002 |
| WO | 03037424 | 5/2003 |
| WO | 03063946 | 8/2003 |
| WO | 03063952 | 8/2003 |
| WO | 03063953 | 8/2003 |
| WO | 03063955 | 8/2003 |
| WO | 03063956 | 8/2003 |
| WO | 03063957 | 8/2003 |
| WO | 2005081784 | 9/2005 |
| WO | 2005102445 | 11/2005 |
| WO | 2005102446 | 11/2005 |
| WO | 2005102447 | 11/2005 |
| WO | 2005115531 | 12/2005 |
| WO | 2006093685 | 9/2006 |
| WO | 2007047966 | 4/2007 |
| WO | 2007089988 | 8/2007 |
| WO | 2007102893 | 9/2007 |
| WO | 2007145671 | 12/2007 |
| WO | 2008077037 | 6/2008 |
| WO | 2008111986 | 9/2008 |
| WO | 2010008833 | 1/2010 |

OTHER PUBLICATIONS

Roger Christoph Luchinger, Safety Aspects of Cardiac Pacemakers in Magnetic Resonance Imaging, a dissertation submitted to the Swiss Federal Institute of Technology Zurich, Zurich, Switzerland, 2002.

(56) References Cited

OTHER PUBLICATIONS

C. Gabriel, S. Gabriel and E. Cortout, I. Dielectric Properties of Biological Tissues: Literature Survey.
S. Gabriel, R.W. Lau and C. Gabriel, II. Dielectric Properties of Biological Tissues: Measurements and the Frequency Range 0Hz to 20 GHz.
S. Gabriel, R.W. Lau and C. Gabriel, III. Dielectric Properties of Biological Tissues: Parametric Models for the Dielectric Spectrum of Tissues.
Constatine A. Balanis, Advanced Engineering Electromagnetics, John Wiley & Sons, Inc., 1989.
Robert C. Susil, Christopher J. Yeung, Henry R. Halperin, Albert CL. Lardo, Ergin Atalar, Multifunctional Interventional Devices for MRI: A Combined Electrophysiology/MRI Catheter, Magnetic Resonance in Medicine, 2002, pp. 594-600, Wiley-Liss, Inc., Departments of Biomedical Engineering, Radiology & Medicine, Johns Hopkins University School of Medicine, Baltimore, Maryland.
Robert C. Susil, Ergin Atalar, Albert Lardo, Multifunctional Interventional Devices for Use in MRI, Provisional U.S. Appl. No. 60/283,725, filed Apr. 13, 2001.
European Search Report dated Oct. 10, 2012.
European Search Report dated Sep. 19, 2012.
Mauritis K. Konings, Lambertus W. Bartels, Henk F.M. Smits and Chris J.G. Bakker, "Heating around Intravascular Guidewires by Resonating RF Waves," Journal of Magnetic Resonance Imaging, 12:79-85, 2000.
Michael J. Weiner, Wilson Greatbatch, Patrick R. Connelly, Provisonal U.S. Appl. No. 60/269,817, filed Feb. 20, 2001, entitled "Electromagnetic Interference Immune Cardiac Assist System."
Wes Clement et al., "Estimation of Effective Lead Loop Area for Implantable Pulse Generators and Implantable Cardioverter Defibrillators," AAMI EMC Task Force, Apr. 12, 2004, 10 pages.
Frank G. Shellock, Ph.D. "MRI Issues for Neuromodulation Devices," Institute for Magnetic Resonance Safety, Education, and Research (IMRSER).
R.S. Johnson et al., Characterization of the Relationship between MR-Induced Distal tip Heating in Cardiac Pacing Leads and the Electrical Performance of Novel Filtered Tip Assemblies; 17th Scientific Meeting & Exhibition of the INternational Society for Magnetic Resonance in Medicine, Honolulu, Hawaii, Apr. 18-24, 2009, p. 307.
F.G. Shellock et al., Comparative Analysis of Mr-Induced Distal Heating in Novel Filtered Cardiac Pacing Leads Using Two Geometric Configurations; 17th Scientific Meeting & Exhibition of the International Society for Magnetic Resonance in Medicine, Honolulu, Hawaii, Apr. 18-24, 2009, p. 3104.
G.D. Wilk et al, High-k Gate Dielectrics: Current Status and Materials Properties Considerations, Journal of Applied Physics, vol. 89, No. 10, May 15, 2001, pp. 5243-5275, 2001 American Physics.

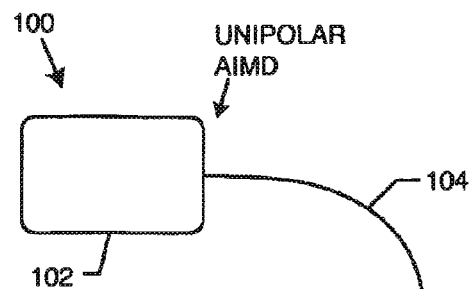
FIG. 8
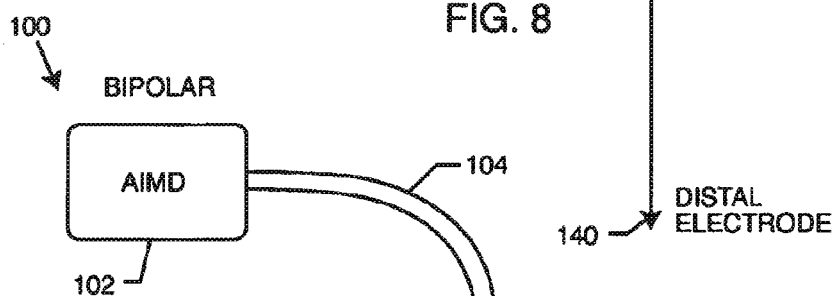
FIG. 9
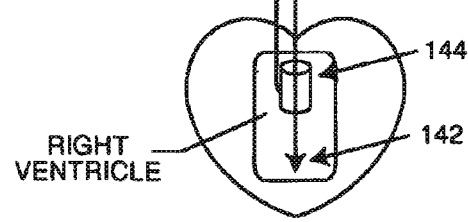
FIG. 10
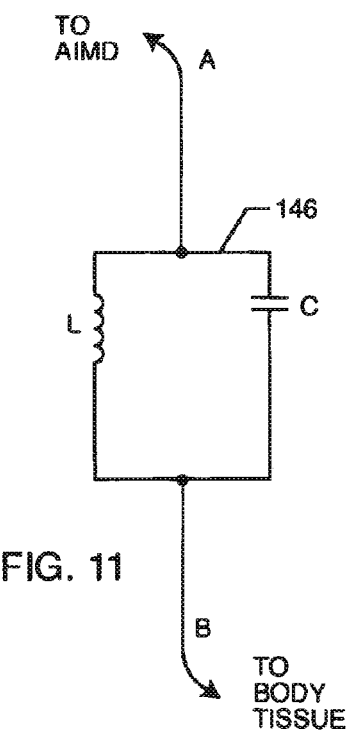
FIG. 11

$$fr = \frac{1}{2\pi\sqrt{LC}}$$

Where: fr = resonant frequency
L = inductance in henries
C = capacitance in farads Solving for C:  Solving for L:

$$C = \frac{1}{(fr)^2(2\pi)^2 L} \qquad L = \frac{1}{(fr)^2(2\pi)^2 C}$$

→ assume a 1.5 Tesla MRI System,
then the RF pulsed frequency = 64 MHz

→ assume that L = 1 nanohenry ($1 \times 10^{-9}$)

then; $C = \dfrac{1}{(64 \times 10^6)^2 (2\pi)^2 (1 \times 10^{-9})}$ or; $C = 6.18 \times 10^{-9}$ f (6.18 nanofared)

$C \approx 6$ nf

FIG. 12

FIG. 14 $\quad z_{ab} = \dfrac{(j\omega L)(-j/\omega C)}{(j\omega L - j/\omega C)}$ FIG. 15 $\quad \begin{array}{l} X_L = +j(2\pi fL) = +j\omega L \\ X_C = -j\left(\dfrac{1}{2\pi fC}\right) = \dfrac{-j}{\omega C} \end{array}$

BAND STOP FILTER COMPRISING AN INDUCTIVE COMPONENT DISPOSED IN A LEAD WIRE IN SERIES WITH AN ELECTRODE

CROSS-REFERENCE TO RELATED APPLICATIONS

This application is a continuation of U.S. patent application Ser. No. 12/170,811, filed on Feb. 4, 2013, which is a divisional of U.S. patent application Ser. No. 11/423,073, filed on Jun. 8, 2006, now U.S. Pat. No. 8,244,370, which is a continuation-in-part of U.S. patent application Ser. No. 10/123,534, filed on Apr. 15, 2002, now U.S. Pat. No. 7,844,319, which claims priority from U.S. Provisional App. Ser. No. 60/283,725, filed on Apr. 13, 2001.

BACKGROUND OF THE INVENTION

This invention relates generally to novel EMI tank filter assemblies, particularly of the type used in active medical devices (AMDs) such as cardiac pacemakers, cardioverter defibrillators, neurostimulators, externally worn Holter monitors and the like, which decouple lead wires and/or electronic components of the medical device from undesirable electromagnetic interference (EMI) signals at a selected frequency or frequencies, such as the RF pulsed fields of Magnetic Resonance Imaging (MRI) equipment.

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contra-indicated with pacemakers and implantable defibrillators. See also:
(1) "Safety Aspects of Cardiac Pacemakers in Magnetic Resonance Imaging", a dissertation submitted to the Swiss Federal Institute of Technology Zurich presented by Roger Christoph Lüchinger, Zurich 2002;
(2) "I. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, Patent Application Publication US 2003/0050557, Susil and Halperin et. al, published Mar. 13, 2003;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, U.S. Patent Application Ser. No. 60/283,725, filed Apr. 13, 2001.
The contents of the foregoing are all incorporated herein by reference.

However, an extensive review of the literature indicates that MRI is indeed often used with pacemaker, neurostimulator and other active implantable medical device (AIMD) patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted lead wires or devices. For example, for magnetic resonance imaging devices operating at the same magnetic field strength and also at the same SAR level, considerable variations have been found relative to heating of implanted lead wires. It is speculated that SAR level alone is not a good predictor of whether or not an implanted device or its associated lead wire system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the recent International Society for Magnetic Resonance in Medicine (ISMRM), which was held on 5 and 6 Nov. 2005, it was reported that certain research systems are going up as high as 11.7 Tesla and will be ready sometime in 2006. This is over 100,000 times the magnetic field strength of the earth. A static magnetic field can induce powerful mechanical forces and torque on any magnetic materials implanted within the patient. This would include certain components within the cardiac pacemaker itself and or lead wire systems. It is not likely (other than sudden system shut down) that the static MRI magnetic field can induce currents into the pacemaker lead wire system and hence into the pacemaker itself. It is a basic principle of physics that a magnetic field must either be time-varying as it cuts across the conductor, or the conductor itself must move within the magnetic field for currents to be induced.

The second type of field produced by magnetic resonance imaging is the pulsed RF field which is generated by the body coil or head coil. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength. The frequency of the RF pulse varies with the field strength of the main static field where: RF PULSED FREQUENCY in MHz=(42.56) (STATIC FIELD STRENGTH IN TESLA).

The third type of electromagnetic field is the time-varying magnetic gradient fields designated $B_1$ which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and EMI are induced into an implanted lead wire system. At very low frequency (VLF), voltages are induced at the input to the cardiac pacemaker as currents circulate throughout the patient's body and create voltage drops. Because of the vector displacement between the pacemaker housing and, for example, the TIP electrode, voltage drop across the resistance of body tissues may be sensed due to Ohms Law and the circulating current of the RF signal. At higher frequencies, the implanted lead wire systems actually act as antennas where currents are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the lead wire system (for example, at the header block of a cardiac pacemaker). This has to do with the wavelength of the signals involved and where they couple efficiently into the system.

Magnetic field coupling into an implanted lead wire system is based on loop areas. For example, in a cardiac pacemaker, there is a loop formed by the lead wire as it comes from the cardiac pacemaker housing to its distal TIP, for example, located in the right ventricle. The return path is through body fluid and tissue generally straight from the TIP electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal implant, the implanted loop area is much larger (greater than 450 square centimeters).

Relating now to the specific case of MRI, the magnetic gradient fields would be induced through enclosed loop areas. However, the pulsed RF fields, which are generated by the body coil, would be primarily induced into the lead wire system by antenna action.

There are a number of potential problems with MRI, including:

(1) Closure of the Pacemaker Reed Switch.

A pacemaker reed switch, which can also be a Hall Effect device, is designed to detect a permanent magnet held close to the patient's chest. This magnet placement allows a physician or even the patient to put the implantable medical device into what is known as the "magnet mode response," The "magnet mode response" varies from one manufacturer to another, however, in general, this puts the pacemaker into a fixed rate or asynchronous pacing mode. This is normally done for short times and is very useful for diagnostic and clinical purposes. However, in some cases, when a pacemaker is brought into the bore or close to the MRI scanner, the MRI static field can make the pacemaker's internal reed switch close, which puts the pacemaker into a fixed rate or asynchronous pacing mode. Worse yet, the reed switch may bounce or oscillate. Asynchronous pacing may compete with the patient's underlying cardiac rhythm. This is one reason why patients have generally been advised not to undergo MRI. Fixed rate or asynchronous pacing for most patients is not an issue. However, in patients with unstable conditions, such as myocardial ischemia, there is a substantial risk for ventricular fibrillation during asynchronous pacing. In most modern pacemakers the magnetic reed switch (or Hall Effect device) function is programmable. If the magnetic reed switch response is switched off, then synchronous pacing is still possible even in strong magnetic fields. The possibility to open and re-close the reed switch in the main magnetic field by the gradient field cannot be excluded. However, it is generally felt that the reed switch will remain closed due to the powerful static magnetic field. It is theoretically possible for certain reed switch orientations at the gradient field to be capable of repeatedly closing and re-opening the reed switch.

(2) Reed Switch Damage.

Direct damage to the reed switch is theoretically possible, but has not been reported in any of the known literature. In an article written by Roger Christoph Lüchinger of Zurich, he reports on testing in which reed switches were exposed to the static magnetic field of MRI equipment. After extended exposure to these static magnetic fields, the reed switches functioned normally at close to the same field strength as before the test.

(3) Pacemaker Displacement.

Some parts of pacemakers, such as the batteries and reed switch, contain ferrous magnetic materials and are thus subject to mechanical forces during MRI. Pacemaker displacement may occur in response to magnetic force or magnetic torque. There are several recent reports on modern pacemakers and ICDs that force and torque are not of concern for MRI systems up to 3 Tesla.

(4) Radio Frequency Field.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and its associated lead wire(s). For example, it will make a difference how much current is induced into a pacemaker lead wire system as to whether it is a left or right pectoral implant. In addition, the routing of the lead and the lead length are also very critical as to the amount of induced current and heating that would occur. Also, distal TIP design is very important as the distal TIP itself can act as its own antenna wherein eddy currents can create heating. The cause of heating in an MRI environment is two fold: (a) RF field coupling to the lead can occur which induces significant local heating; and (b) currents induced between the distal TIP and tissue during MRI RF pulse transmission sequences can cause local Ohms Law heating in tissue next to the distal TIP electrode of the implanted lead. The RF field of an MRI scanner can produce enough energy to induce lead wire currents sufficient to destroy some of the adjacent myocardial tissue. Tissue ablation has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD lead wire geometries. There can also be localized heating problems associated with various types of electrodes in addition to TIP electrodes. This includes RING electrodes or PAD electrodes. RING electrodes are commonly used with a wide variety of implanted devices including cardiac pacemakers, neurostimulators, probes, catheters and the like. PAD electrodes are very common in neurostimulator applications. For example, spinal cord stimulators or deep brain stimulators can include a plurality of PAD electrodes to make contact with nerve tissue. A good example of this also occurs in a cochlear implant. In a typical cochlear implant there would be sixteen RING electrodes that the position places by pushing the electrode up into the cochlea. Several of these RING electrodes make contact with auditory nerves.

(5) Alterations of Pacing Rate Due to the Applied Radio Frequency Field.

It has been observed that the RF field may induce undesirable fast pacing (QRS complex) rates. There are various mechanisms which have been proposed to explain rapid pacing: direct tissue stimulation, interference with pacemaker electronics or pacemaker reprogramming (or reset). In all of these cases, it is very desirable to raise the lead system impedance (at the MRI RF pulsed frequency) to make an EMI filter feedthrough capacitor more effective and thereby provide a higher degree of protection to AIMD electronics. This will make alterations in pacemaker pacing rate and/or pacemaker reprogramming much more unlikely.

(6) Time-Varying Magnetic Gradient Fields.

The contribution of the time-varying gradient to the total strength of the MRI magnetic field is negligible, however, pacemaker systems could be affected because these fields are rapidly applied and removed. The time rate of change of the magnetic field is directly related to how much electromagnetic force and hence current can be induced into a lead wire system. Lüchinger reports that even using today's gradient systems with a time-varying field up to 50 Tesla per second, the induced currents are likely to stay below the biological thresholds for cardiac fibrillation. A theoretical upper limit for the induced voltage by the time-varying magnetic gradient field is 20 volts. Such a voltage during more than 0.1 milliseconds could be enough energy to directly pace the heart.

(7) Heating.

Currents induced by time-varying magnetic gradient fields may lead to local heating. Researchers feel that the calculated heating effect of the gradient field is much less as compared to that caused by the RF field and therefore for the purposes herein may be neglected.

There are additional problems possible with implantable cardioverter defibrillators (ICDs). ICDs use different and larger batteries which could cause higher magnetic forces. The programmable sensitivity in ICDs is normally much higher (more sensitive) than it is for pacemakers, therefore, ICDs may falsely detect a ventricular tacchyarrhythmia and inappropriately deliver therapy. In this case, therapy might include anti-tacchycardia pacing, cardio version or defibrillation (high voltage shock) therapies. MRI magnetic fields may prevent detection of a dangerous ventricular arrhythmia or fibrillation. There can also be heating problems of ICD leads which are expected to be comparable to those of pacemaker leads. Ablation of vascular walls is another concern. Fortunately, ICDs have a sort of built-in fail-safe mechanism. That is, during an MRI procedure, if they inadvertently sense the MRI fields as a dangerous ventricular arrhythmia, the ICD will attempt to charge up and deliver a high voltage shock. However, there is a transformer contained within the ICD that is necessary to function in order to charge up the high-energy storage capacitor contained within the ICD. In the presence of the main static field of the MRI the core of this transformer tends to saturate thereby preventing the high voltage capacitor from charging up. This makes it highly unlikely that an ICD patient undergoing an MRI would receive an inappropriate high voltage shock therapy. While ICDs cannot charge during MRI due to the saturation of their ferro-magnetic transformers, the battery will be effectively shorted and lose life. This is a highly undesirable condition.

In summary, there are a number of studies that have shown that MRI patients with active implantable medical devices, such as cardiac pacemakers, can be at risk for potential hazardous effects. However, there are a number of reports in the literature that MRI can be safe for imaging of pacemaker patients when a number of precautions are taken (only when an MRI is thought to be an absolute diagnostic necessity). These anecdotal reports are of interest, however, they are certainly not scientifically convincing that all MRI can be safe. As previously mentioned, just variations in the pacemaker lead wire length can significantly effect how much heat is generated. From the layman's point of view, this can be easily explained by observing the typical length of the antenna on a cellular telephone compared to the vertical rod antenna more common on older automobiles. The relatively short antenna on the cell phone is designed to efficiently couple with the very high frequency wavelengths (approximately 950 MHz) of cellular telephone signals. In a typical AM and FM radio in an automobile, these wavelength signals would not efficiently couple to the relatively short antenna of a cell phone. This is why the antenna on the automobile is relatively longer. An analogous situation exists with an AIMD patient in an MRI system. If one assumes, for example, a 3.0 Tesla MRI system, which would have an RF pulsed frequency of 128 MHz, there are certain implanted lead lengths that would couple efficiently as fractions of the 128 MHz wavelength. It is typical that a hospital will maintain an inventory of various leads and that the implanting physician will make a selection depending on the size of the patient, implant location and other factors. Accordingly, the implanted or effective lead wire length can vary considerably. There are certain implanted lead wire lengths that just do not couple efficiently with the MRI frequency and there are others that would couple very efficiently and thereby produce the worst case for heating.

The effect of an MRI system on the function of pacemakers, ICDs and neurostimulators depends on various factors, including the strength of the static magnetic field, the pulse sequence (gradient and RF field used), the anatomic region being imaged, and many other factors. Further complicating this is the fact that each patient's condition and physiology is different and each manufacturer's pacemaker and ICD designs also are designed and behave differently. Most experts still conclude that MRI for the pacemaker patient should not be considered safe. Paradoxically, this also does not mean that the patient should not receive MRI. The physician must make an evaluation given the pacemaker patient's condition and weigh the potential risks of MRI against the benefits of this powerful diagnostic tool. As MRI technology progresses, including higher field gradient changes over time applied to thinner tissue slices at more rapid imagery, the situation will continue to evolve and become more complex. An example of this paradox is a pacemaker patient who is suspected to have a cancer of the lung. RF ablation treatment of such a tumor may require stereotactic imaging only made possible through real time fine focus MRI. With the patient's life literally at risk, the physician with patient informed consent may make the decision to perform MRI in spite of all of the previously described attendant risks to the pacemaker system.

Insulin drug pump systems do not seem to be of a major current concern due to the fact that they have no significant antenna components (such as implanted lead wires). However, some implantable pumps work on magneto-peristaltic systems, and must be deactivated prior to MRI. There are newer (unreleased) systems that would be based on solenoid systems which will have similar problems.

It is clear that MRI will continue to be used in patients with both external and active implantable medical devices. There are a number of other hospital procedures, including electrocautery surgery, lithotripsy, etc., to which a pacemaker patient may also be exposed. Accordingly, there is a need for AIMD system and/or circuit protection devices which will improve the immunity of active implantable medical device systems to diagnostic procedures such as MRI.

As one can see, many of the undesirable effects in an implanted lead wire system from MRI and other medical diagnostic procedures are related to undesirable induced currents in the lead wire system and/or its distal TIP (or RING). This can lead to overheating either in the lead wire or at the body tissue at the distal TIP. For a pacemaker application, these currents can also directly stimulate the heart into sometimes dangerous arrhythmias.

Accordingly, there is a need for a novel resonant tank band stop filter assembly which can be placed at various locations along the active implantable medical device lead wire system, which also prevents current from circulating at selected frequencies of the medical therapeutic device. Preferably, such novel tank filters would be designed to resonate at 64 MHz for use in an MRI system operating at 1.5 Tesla (or 128 MHz for a 3 Tesla system). The present invention fulfills these needs and provides other related advantages.

SUMMARY OF THE INVENTION

The present invention comprises resonant tank circuits/band stop filters to be placed at one or more locations along the active medical device (AMD) lead wire system, including its distal Tip. These band stop filters prevent current from circulating at selected frequencies of the medical therapeutic device. For example, for an MRI system operating at 1.5 Tesla, the pulse RF frequency is 64 MHz. The novel band stop filters of the present invention can be designed to resonate at 64 MHz and thus create an open circuit in the lead wire system at that selected frequency. For example, the band stop filter of the present invention, when placed at the distal TIP, will prevent currents from flowing through the distal TIP, prevent currents from flowing in the lead wires and also prevent currents from flowing into body tissue. It will be obvious to those skilled in the art that all of the embodiments described herein are equally applicable to a wide range of other active implantable or external medical devices, including deep brain stimulators, spinal cord stimulators, cochlear implants, ventricular assist devices, artificial hearts, drug pumps, Holter monitors and the like. The present invention fulfills all of the needs regarding reduction or elimination of undesirable currents and associated heating in implanted lead wire systems. The band stop filter structures as described herein also have a broad application to other fields, including telecommunications, military, space and the like.

Electrically engineering a capacitor in parallel with an inductor is known as a tank filter. It is also well known that when the tank filter is at its resonant frequency, it will present a very high impedance. This is a basic principle of all radio receivers. In fact, multiple tank filters are often used to improve the selectivity of a radio receiver. One can adjust the resonant frequency of the tank circuit by either adjusting the capacitor value or the inductor value or both. Since medical diagnostic equipment which is capable of producing very large fields operates at discrete frequencies, this is an ideal situation for a specific tank or band stop filter. Band stop filters are more efficient for eliminating one single frequency than broadband filters. Because the band stop filter is targeted at this one frequency or range of frequencies, it can be much smaller and volumetrically efficient. In addition, the way MRI RF pulse fields couple with lead wire systems, various loops and associated loop currents result along various sections of the lead wire. For example, at the distal TIP of a cardiac pacemaker, direct electromagnetic forces (EMF) can be produced which result in current loops through the distal TIP and into the associated myocardial tissue. This current system is largely decoupled from the currents that are induced near the active implantable medical device, for example, near the cardiac pacemaker. There the MRI may set up a separate loop with its associated currents. Accordingly, one or more band stop filters may be required to completely control all of the various induced EMI and associated currents in a lead wire system.

The present invention which resides in band stop filters is also designed to work in concert with the EMI filter which is typically used at the point of lead wire ingress and egress of the active implantable medical device. For example, see U.S. Pat. No. 5,333,095, entitled FEEDTHROUGH FILTER CAPACITOR ASSEMBLY FOR HUMAN IMPLANT; U.S. Pat. No. 6,999,818, entitled INDUCTOR CAPACITOR EMI FILTER FOR HUMAN IMPLANT APPLICATIONS; U.S. patent application Ser. No. 11/097,999 filed Mar. 31, 2005, entitled APPARATUS AND PROCESS FOR REDUCING THE SUSCEPTIBILITY OF ACTIVE IMPLANTABLE MEDICAL DEVICES TO MEDICAL PROCEDURES SUCH AS MAGNETIC RESONANCE IMAGING; and U.S. patent application Ser. No. 11/163,915 filed Nov. 3, 2005, entitled PROCESS FOR TUNING AN EMI FILTER TO REDUCE THE AMOUNT OF HEAT GENERATED IN IMPLANTED LEAD WIRES DURING MEDICAL PROCEDURES SUCH AS MAGNETIC RESONANCE IMAGING; the contents of all being incorporated herein by reference. All of these patent documents describe novel inductor capacitor combinations for low pass EMI filter circuits. It is of particular interest that by increasing the number of circuit elements, one can reduce the overall capacitance value which is at the input to the implantable medical device. It is important to reduce the capacitance value to raise the input impedance of the active implantable medical device such that this also reduces the amount of current that would flow in lead wire systems associated with medical procedures such as MRI. Accordingly, it is a feature of the present invention that the novel band stop filters are designed to be used in concert with the structures described in the above mentioned three patent applications.

As described in U.S. Patent Publication No. 2003/0050557 and U.S. Patent Application Ser. No. 60/283,725, the present invention is also applicable to probes and catheters. For example, ablation probes are used to selectively cauterize or ablate tissue on the inside or outside of the heart to control erratic electrical pulses. These procedures are best performed during real time fluoroscopy or MRI imaging. However, a major concern is the overheating of the distal TIP at inappropriate times because of the induced currents from the MRI system. It will be obvious to one skilled in the art that the novel band stop filters of the present invention can be adapted to any probe, TIP or catheter that is used in the human body.

Moreover, the present invention is also applicable to a number of external leads that might be placed on a patient during MRI. For example, patients frequently wear Holter monitors to monitor their cardiac activity over a period of days. It is an aggravation to physicians to have a patient sent up to the MRI Department and have all these carefully placed electrodes removed from the patient's body. Typically the MRI technicians are concerned about leaving these leads on during an MRI because they don't want them to overheat and cause surface burns on the patient's skin. The problem is that after the MRI procedure, the MRI technicians often replace these electrodes or skin patches in different or even in the wrong locations. This greatly confounds the cardiac physician because now the Holter monitor results are no longer consistent. It is a feature of the present invention that the tank filters could be placed in any externally worn lead wires by the patient during an MRI procedure such that they do not need to be removed.

In one embodiment, the invention provides a medical therapeutic device comprising an active medical device (AMD), a lead wire extending from the AMD to a distal TIP thereof, and a band stop filter associated with the lead wire for attenuating current flow through the lead wire at a selected frequency.

The AMD may comprise cochlear implants, piezoelectric sound bridge transducers, neurostimulators, brain stimulators, cardiac pacemakers, ventricular assist devices, artificial hearts, drug pumps, bone growth stimulators, bone fusion stimulators, urinary incontinence devices, pain relief spinal cord stimulators, anti-tremor stimulators, gastric stimulators, implantable cardioverter defibrillators, pH probes, congestive heart failure devices, pill cameras, neuromodulators, cardiovascular stents, orthopedic implants, external insulin pumps, external drug pumps, external neurostimulators; and external probes or catheters.

The band stop filter itself comprises a capacitor (and its resistance or an added resistance) in parallel with an inductor (and its parasitic resistance), said parallel capacitor and inductor combination being placed in series with the medical device lead wire(s) wherein the values of capacitance and inductance have been selected such that the band stop filter is resonant at a selected frequency (such as the MRI pulsed frequency).

In the preferred embodiment, the Q of the inductor is relatively maximized and the Q of the capacitor is relatively minimized to reduce the overall Q of the band stop filter. The Q of the inductor is relatively maximized by minimizing the parasitic resistive loss in the inductor, and the Q of the capacitor is relatively minimized by raising its equivalent series resistance (ESR) of the capacitor (or by adding resistance or a resistive element in series with the capacitor element of the bank stop tank filter). This reduces the overall Q of the band stop filter in order to broaden its 3 dB points and thereby attenuate current flow through the lead wire along a range of selected frequencies. In AIMD or external medical device applications, the range of selected frequencies includes a plurality of MRI pulsed frequencies.

The equivalent series resistance of the capacitor is raised by any of the following: reducing thickness of electrode plates in the capacitor; using higher resistivity capacitor electrode materials, providing apertures, gaps, slits or spokes in the electrode plates of the capacitor; providing separate discrete resistors in series with the capacitor; utilizing resistive electrical attachment materials to the capacitor; or utilizing capacitor dielectric materials that have high dielectric loss tangents at the selected frequency. Methods of using higher resistivity capacitor electrode materials include, for example, using platinum instead of silver electrodes. Platinum has a higher volume resistivity as compared to pure silver. Another way of reducing capacitor electrode plate resistivity is to add ceramic powders to the electrode ink before it is silk screened down and fired. After firing, this has the effect of separating the conductive electrode portions by insulative dielectric areas which increases the overall resistivity of the electrode plate.

As defined herein, raising the capacitor ESR includes any or all of the above described methods of adding resistance in series with the capacitive element of the band stop filter. It should be noted that deliberately raising the capacitor ESR runs counter to conventional/prior art capacitor technologies. In fact, capacitor manufacturers generally strive to build capacitors with as low an ESR as possible. This is to minimize energy loss, etc. It is a feature of the present invention that capacitor Q is raised in a controlled manner in the tank filter circuit in order to adjust its Q and adjust the band stop frequency width in the range of MRI pulsed frequencies.

Preferably, the band stop filter is disposed adjacent to the distal tip of the lead wire and is integrated into a TIP electrode. It may also be integrated into one or more RING electrodes. The lead wire may also comprise an externally worn lead wire, or it may come from an externally worn electronics module wherein said lead penetrates through the skin surface to an implanted distal electrode.

The present invention also provides a novel process for attenuating current flow through a lead wire for an active medical device at a selected frequency, comprising the steps of: selecting a capacitor which is resonant at the selected frequency; selecting an inductor which is resonant at the selected frequency; using the capacitor and the inductor to form a tank filter circuit; and placing the tank filter circuit in series with the lead wire.

The overall Q of the tank filter circuit may be reduced by increasing the Q of the inductor and reducing the Q of the capacitor. In this regard, minimizing resistive loss in the inductor maximizes the Q of the inductor, and raising the equivalent series resistance of the capacitor minimizes the Q of the capacitor.

The net effect is to reduce the overall Q of the tank filter circuit which widens the band stop width to attenuate current flow through the lead wire along a range of selected frequencies. As discussed herein, the range of selected frequencies may include a plurality of MRI pulse frequencies.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 8 is a diagram of a unipolar active implantable medical device;

FIG. 9 is a diagram similar to FIG. 8, illustrating a bipolar AIMD system;

FIG. 10 is a diagram similar to FIGS. 8 and 9, illustrating a biopolar lead wire system with a distal TIP and RING, typically used in a cardiac pacemaker;

FIG. 11 is a schematic diagram showing a parallel combination of an inductor L and a capacitor C placed in series with the lead wire systems of FIGS. 8-10;

FIG. 12 is a chart illustrating calculation of frequency of resonance for the parallel tank circuit of FIG. 11;

FIG. 14 is an equation for the impedance of an inductor in parallel with a capacitor;

FIG. 15 is a chart illustrating reactance equations for the inductor and the capacitor of the parallel tank circuit of FIG. 11;

DETAILED DESCRIPTION OF THE PREFERRED EMBODIMENT

Figure 1:
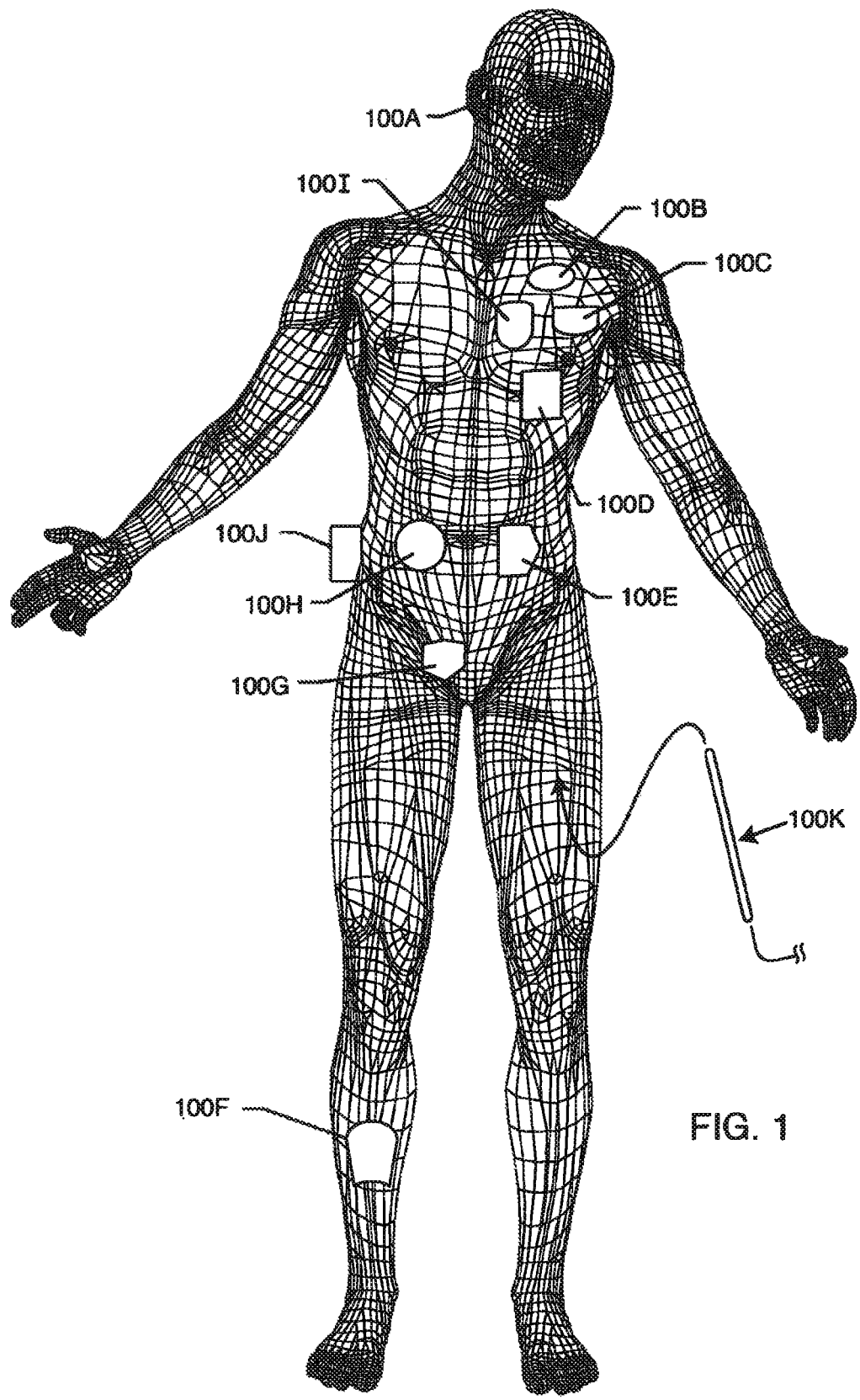
FIG. 1 is a wire-formed diagram of a generic human body showing a number of active implantable medical devices (AIMDs)

FIG. 1 illustrates of various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. The lead wires that come from a deep brain stimulator are often placed using real time imaging. Most commonly such lead wires are placed during real time MRI. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise knows as CRT devices. 100J illustrates an externally worn pack. This pack could be an external insulin pump, an external drug pump, an external neurostimulator, a Holter monitor with skin electrodes or even a ventricular assist device power pack. 100K illustrates the insertion of an external probe or catheter. These probes can be inserted into the femoral artery, for example, or in any other number of locations in the human body.

Figure 2:
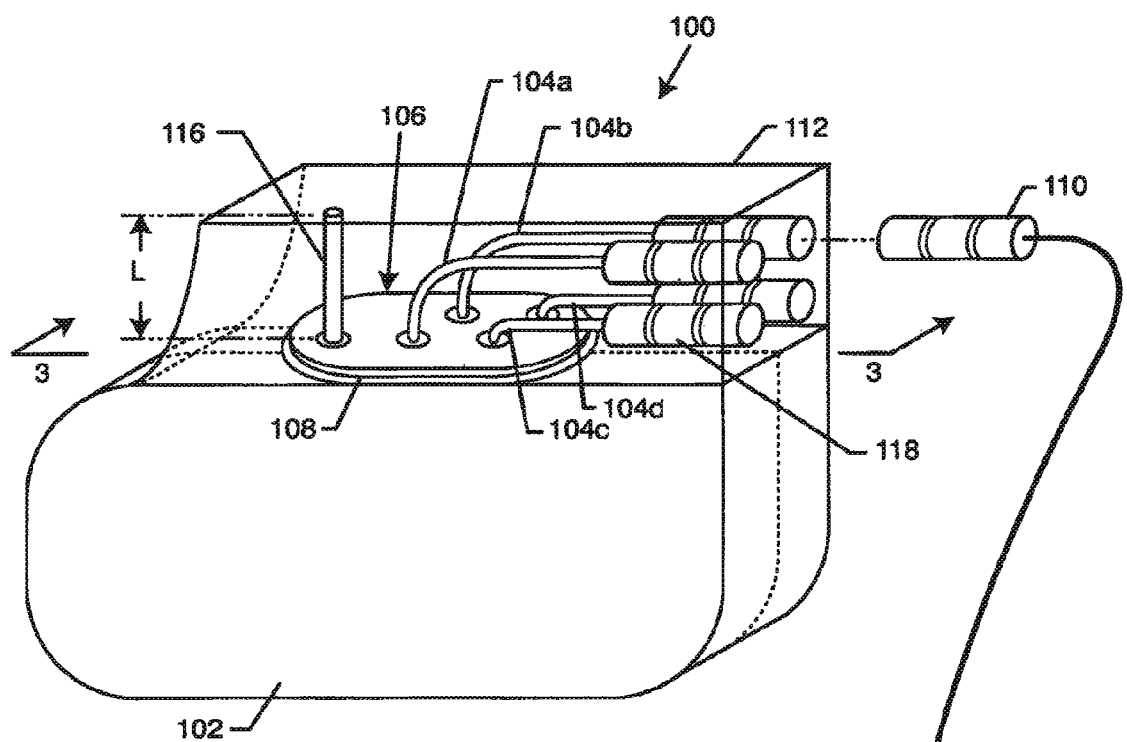
FIG. 2 is a perspective and somewhat schematic view of a prior art active implantable medical device (AIMD) including a lead wire directed to the heart of a patient.

Referring now to FIG. 2, a prior art active implantable medical device (AIMD) 100 is illustrated. In general, the AIMD 100 could, for example, be a cardiac pacemaker 100C which is enclosed by a titanium housing 102 as indicated. The titanium housing is hermetically sealed, however there is a point where lead wires 104 must ingress and egress the hermetic seal. This is accomplished by providing a hermetic terminal assembly 106. Hermetic terminal assemblies are well known and generally consist of a ferrule 108 which is laser welded to the titanium housing 102 of the AIMD 100. The hermetic terminal assembly 106 with its associated EMI filter is better shown in FIG. 3. Referring once again to FIG. 2, four lead wires are shown consisting of lead wire pair 104a and 104b and lead wire pair 104c and 104d. This is typical of what's known as a dual chamber bipolar cardiac pacemaker.

The IS1 connectors 110 that are designed to plug into the header block 112 are low voltage (pacemaker) connectors covered by an ANSI/AAMI standard IS-1. Higher voltage devices, such as implantable cardioverter defibrillators, are covered by a standard known as the ANSI/AAMI DF-1. There is a new standard under development which will integrate both high voltage and low voltage connectors into a new miniature connector series known as the IS-4 series. These connectors are typically routed in a pacemaker application down into the right ventricle and right atrium of the heart 114. There are also new generation devices that have been introduced to the market that couple lead wires to the outside of the left ventricle. These are known as biventricular devices and are very effective in cardiac resynchronization therapy (CRT) and treating congestive heart failure (CHF).

Referring once again to FIG. 2, one can see, for example, the bipolar lead wires 104a and 104b that could be routed, for example, to the distal TIP and RING into the right ventricle. The bipolar lead wires 104c and 104d could be routed to a distal TIP and RING in the right atrium. There is also an RF telemetry pin antenna 116 which is not connected to the IS-1 or DS-1 connector block. This acts as a short stub antenna for picking up telemetry signals that are transmitted from the outside of the device 100.

It should also be obvious to those skilled in the art that all of the descriptions herein are equally applicable to other types of AIMDs. These include implantable cardioverter defibrillators (ICDs), neurostimulators, including deep brain stimulators, spinal cord stimulators, cochlear implants, incontinence stimulators and the like, and drug pumps. The present invention is also applicable to a wide variety of minimally invasive AIMDs. For example, in certain hospital cath lab procedures, one can insert an AIMD for temporary use such as an ICD. Ventricular assist devices also can fall into this type of category. This list is not meant to be limiting, but is only example of the applications of the novel technology currently described herein.

Figure 3:
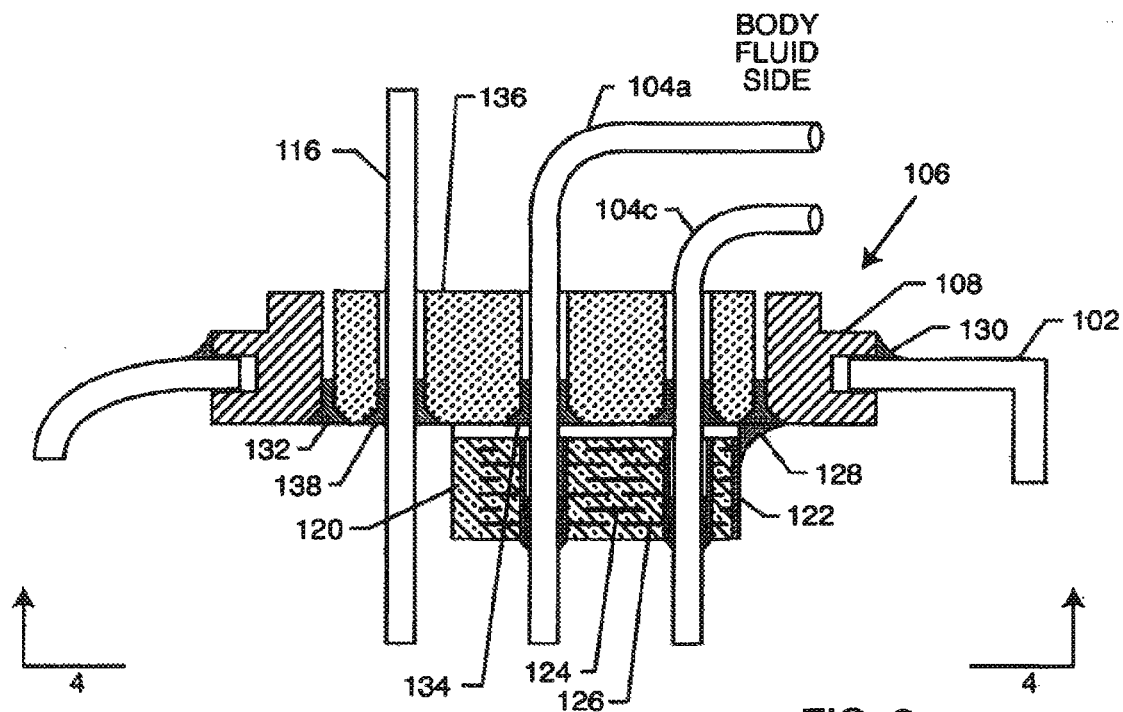
FIG. 3 is an enlarged sectional view taken generally along the line 3-3 of FIG. 2.

FIG. 3 is an enlarged, fragmented cross-sectional view taken generally along line 3-3 of FIG. 2. Here one can see in cross-section the RF telemetry pin 116 and the bipolar lead wires 104a and 104c which would be routed to the cardiac chambers by connecting these lead wires to the internal connectors 118 of the IS-1 header block 112 (FIG. 2). These connectors are designed to receive the plug 110 which allows the physicians to thread lead wires through the venous system down into the appropriate chambers of the heart 114. It will be obvious to those skilled in the art that tunneling of deep brain electrodes or neurostimulators are equivalent.

Referring back to FIG. 3, one can see a prior art feedthrough capacitor 120 which has been bonded to the hermetic terminal assembly 106. These feedthrough capacitors are well known in the art and are described and illustrated in U.S. Pat. Nos. 5,333,095, 5,751,539, 5,978,204, 5,905,627, 5,959,829, 5,973,906, 5,978,204, 6,008,980, 6,159,560, 6,275,369, 6,424,234, 6,456,481, 6,473,291, 6,529,103, 6,566,978, 6,567,259, 6,643,903, 6,675,779, 6,765,780 and 6,882,248. In this case, a rectangular quadpolar feedthrough capacitor 120 is illustrated which has an external metallized termination surface 122. It includes embedded electrode plate sets 124 and 126. Electrode plate set 124 is known as the ground electrode plate set and is terminated at the outside of the capacitor 120 at the termination surface 122. These ground electrode plates 124 are electrically and mechanically connected to the ferrule 108 of the hermetic terminal assembly 106 using a thermosetting conductive polyimide or equivalent material 128 (equivalent materials will include solders, brazes, conductive epoxies and the like). In turn, the hermetic seal terminal assembly 106 is designed to have its titanium ferrule 108 laser welded 130 to the overall housing 102 of the AIMD 100. This forms a continuous hermetic seal thereby preventing body fluids from penetrating into and causing damage to the electronics of the AIMD.

It is also essential that the lead wires 104 and insulator 136 be hermetically sealed, such as by the gold brazes or glass seals 132 and 134. The gold braze 132 wets from the titanium ferrule 108 to the alumina ceramic insulator 136. In turn, the ceramic alumina insulator 136 is also gold brazed at 134 to each of the lead wires 104. The RF telemetry pin 116 is also gold brazed at 138 to the alumina ceramic insulator 136. It will be obvious to those skilled in the art that there are a variety of other ways of making such a hermetic terminal. This would include glass sealing the leads into the ferrule directly without the need for the gold brazes.

As shown in FIG. 3, the RF telemetry pin 116 has not been included in the area of the feedthrough capacitor 120. The reason for this is the feedthrough capacitor 120 is a very broadband single element EMI filter which would eliminate the desirable telemetry frequency.

Figure 4:
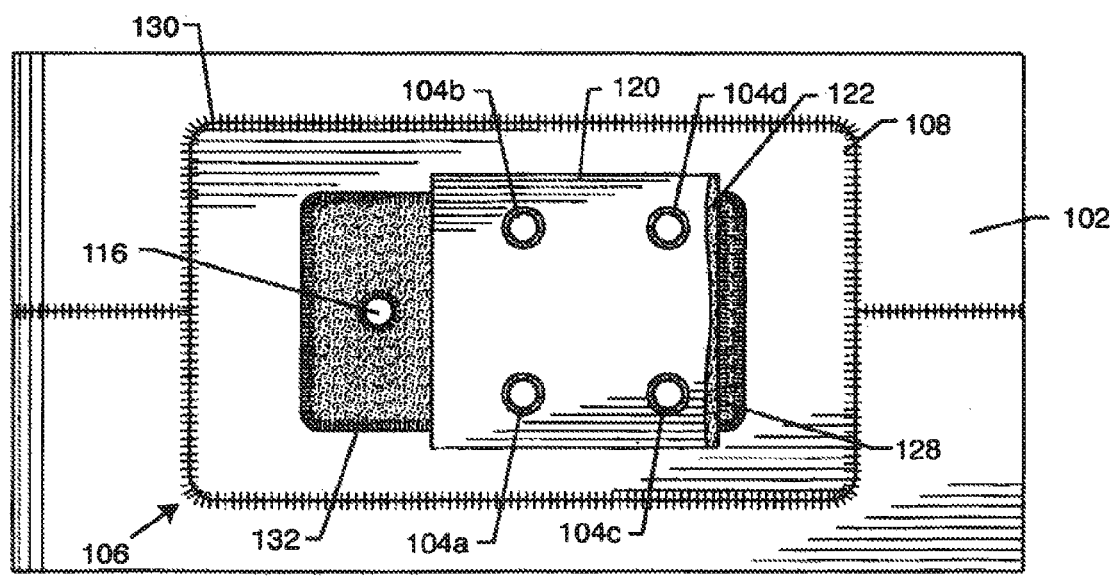
FIG. 4 is a view taken generally along the line 4-4 of FIG. 3.

FIG. 4 is a bottom view taken generally along line 4-4 in FIG. 3. One can see the gold braze 132 which completely seals the hermetic terminal insulator 136 into the overall titanium ferrule 108. One can also see the overlap of the capacitor attachment materials, shown as a thermosetting conductive adhesive 128, which makes contact to the gold braze 132 that forms the hermetic terminal 106.

Figure 5:
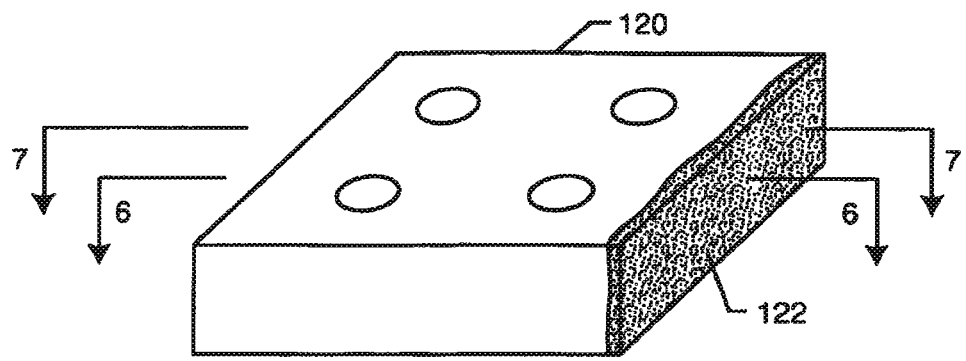
FIG. 5 is a perspective/isometric view of a prior art rectangular quadpolar feedthrough capacitor of the type shown in FIGS. 3 and 4.
Figure 6:
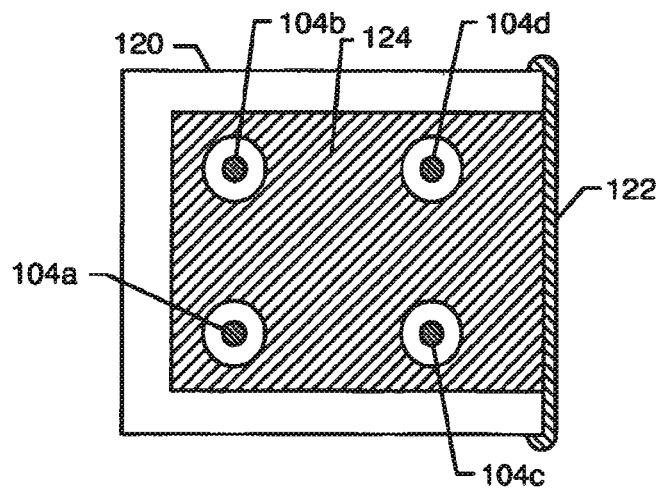
FIG. 6 is sectional view taken generally along the line 6-6 of FIG. 5.
Figure 7:
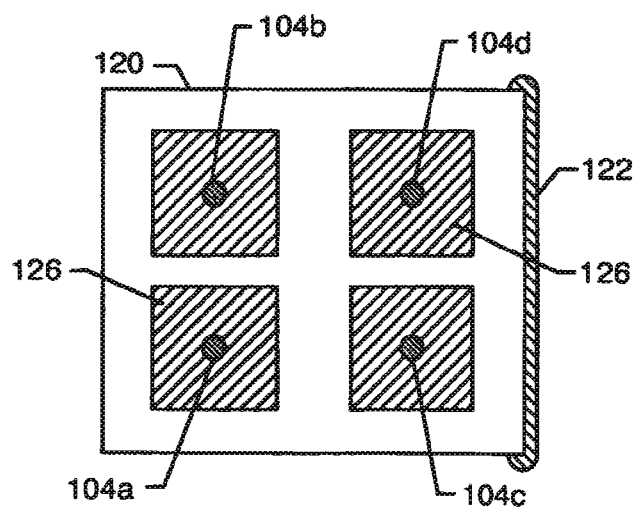
FIG. 7 is a sectional view taken generally along the line 7-7 of FIG. 5.

FIG. 5 is an isometric view of the feedthrough capacitor 120. As one can see, the termination surface 122 connects to the capacitor's internal ground plate set 124. This is best seen in FIG. 6 where ground plate set 124, which is typically silk-screened onto ceramic layers, is brought out and exposed to the termination surface 122. The capacitor's four (quadpolar) active electrode plate sets 126 are illustrated in FIG. 7. In FIG. 6 one can see that the lead wires 104 are in non-electrical communication with the ground electrode plate set 124. However, in FIG. 7 one can see that each one of the lead wires 104 is in electrical contact with its corresponding active electrode plate set 126. The amount of capacitance is determined by the overlap of the active electrode plate area 126 over the ground electrode plate area. One can increase the amount of capacitance by increasing the area of the active electrode plate set 126. One can also increase the capacitance by adding additional layers. In this particular application, we are only showing six electrode layers: three ground plates 124 and three active electrode plate sets 126 (FIG. 3). However, 10, 60 or even more than 100 such sets can be placed in parallel thereby greatly increasing the capacitance value. The capacitance value is also related to the dielectric thickness or spacing between the ground electrode set 124 and the active electrode set 126. Reducing the dielectric thickness increases the capacitance significantly while at the same time reducing its voltage rating. This gives the designer many degrees of freedom in selecting the capacitance value.

In the following description, functionally equivalent elements shown in various embodiments will often be referred to utilizing the same reference number.

FIG. 8 is a general diagram of a unipolar active implantable medical device system 100. FIG. 8 could also be representative of an externally worn medical device such as a Holter monitor. In the case of a Holter monitor, the distal electrode 140 would typically be a scan or patch electrode. The housing 102 of the active implantable medical device 100 is typically titanium, ceramic, stainless steel or the like. Inside of the device housing are the AIMD electronic circuits. Usually AIMDs include a battery, but that is not always the case. For example, for a Bion, it can receive its energy from an external pulsing magnetic field. A lead wire 104 is routed from the AIMD 100 to a point 140 where it is embedded in or affixed to body tissue. In the case of a spinal cord stimulator 100H, the distal TIP 140 could be in the spinal cord. In the case of a deep brain stimulator 100B, the distal electrode 140 would be placed deep into the brain, etc. In the case of a cardiac pacemaker 100C, the distal electrode 140 would typically be placed in the cardiac right ventricle.

FIG. 9 is very similar to FIG. 8 except that it is a bipolar system. In this case, the electric circuit return path is between the two distal electrodes 140 and 140'. In the case of a cardiac pacemaker 100C, this would be known as a bipolar lead wire system with one of the electrodes known as the distal TIP 142 and the other electrode which would float in the blood pool known as the RING 144 (see FIG. 10). In contrast, the electrical return path in FIG. 8 is between the distal electrode 140 through body tissue to the conductive housing 102 of the implantable medical device 100.

FIG. 10 illustrates a bipolar lead wire system with a distal TIP 142 and RING 144 typically as used in a cardiac pacemaker 100C. In all of these applications, the patient could be exposed to the fields of an MRI scanner or other powerful emitter used during a medical diagnostic procedure. Currents that are directly induced in the lead wire system 104 can cause heating by I²R losses in the lead wire system or by heating caused by current flowing in body tissue. If these currents become excessive, the associated heating can cause damage or even destructive ablation to body tissue.

The distal TIP 142 is designed to be implanted into or affixed to the actual myocardial tissue of the heart. The RING 144 is designed to float in the blood pool. Because the blood is flowing and is thermally conductive, the RING 144 structure is substantially cooled. In theory, however, if the lead curves, the RING 144 could also touch and become encapsulated by body tissue. The distal TIP 142, on the other hand, is always thermally insulated by surrounding body tissue and can readily heat up due to the RF pulse currents of an MRI field.

FIG. 11 is a schematic diagram showing a parallel combination of an inductor L and a capacitor C to be placed in the lead wire systems 104 previously described. This combination forms a parallel tank circuit or band stop filter 146 which will resonate at a particular frequency ($f_r$).

FIG. 12 gives the frequency of resonance equation $f_r$ for the parallel tank circuit 146 of FIG. 11: where $f_r$ is the frequency of resonance in hertz, L is the inductance in henries and C is the capacitance in farads. MRI systems vary in static field strength from 0.5 Tesla all the way up to 3 Tesla with newer research machines going much higher. This is the force of the main static magnetic field. The frequency of the pulsed RF field associated with MRI is found by multiplying the static field in Teslas times 42.45. Accordingly, a 3 Tesla MRI system has a pulsed RF field of approximately 128 MHz.

Referring once again to FIG. 11, one can see that if the values of the inductor and the capacitor are selected properly, one could obtain a parallel tank resonant frequency of 128 MHz. For a 1.5 Tesla MRI system, the RF puke frequency is 64 MHz. Referring to FIG. 12, one can see the calculations assuming that the inductor value L is equal to one nanohenry. The one nanohenry comes from the fact that given the small geometries involved inside of the human body, a very large inductor will not be possible. This is in addition to the fact that the use of ferrite materials or iron cores for such an inductor are not practical for two reasons: 1) the static magnetic field from the MRI scanner would align the magnetic dipoles (saturate) in such a ferrite and therefore make the inductor ineffective; and 2) the presence of ferrite materials will cause severe MRI image artifacts. What this means is that if one were imaging the right ventricle of the heart, for example, a fairly large area of the image would be blacked out or image distorted due to the presence of these ferrite materials and the way it interacts with the MRI field. It is also important that the inductance value not vary while in the presence of the main static field.

The relationship between the parallel inductor L and capacitor C is also very important. One could use, for example, a very large value of inductance which would result in a very small value of capacitance to be resonant, for example, at the MRI frequency of 64 MHz. However, using a very high value of inductor results in a high number of turns of very small wire. Using a high number of turns of very small diameter wire is contraindicated for two reasons. The first reason is that the long length of relatively small diameter wire results in a very high DC resistance for the inductor. This resistance is very undesirable because low frequency pacing or neurostimulator pulses would lose energy passing through the relatively high series resistance. This is also undesirable where the AND is sensing biologic signals. For example, in the case of a pacemaker or deep brain stimulator, continuous sensing of low frequency biological signals is required. Too much series resistance in a lead wire system will attenuate such signals thereby making the AIMD less efficient. Accordingly, it is a preferred feature of the present invention that a relatively large value of capacitance will be used in parallel with a relatively small value of inductance, for example, employing highly volumetrically efficient ceramic dielectric capacitors that can create a great deal of capacitance in a very small space.

It should be also noted that below resonance, particularly at very low frequencies, the current in the parallel L-C band width stop filter passes through the inductor element. Accordingly, it is important that the parasitic resistance of the inductor element be quite low. Conversely, at very low frequencies, no current passes through the capacitor element. At high frequencies, the reactance of the capacitor element drops to a very low value. However, as there is no case where it is actually desirable to have high frequencies pass through the tank filter, the parasitic resistive loss of the capacitor is not particularly important. This is also known as the capacitor's equivalent series resistance (ESR). A component of capacitor ESR is the dissipation factor of the capacitor (a low frequency phenomena). Off of resonance, it is not particularly important how high the capacitor's dissipation factor or overall ESR is when used as a component of a parallel tank circuit 146 as described herein. Accordingly, an air wound inductor is the ideal choice because it is not affected by MRI signals or fields. Because of the space limitations, however, the inductor, will not be very volumetrically efficient. For this reason, it is preferable to keep the inductance value relatively low (in the order of 1 to 100 nanohenries).

Referring once again to FIG. 12, one can see the calculations for capacitance by algebraically solving the resonant frequency $f_r$ equation shown for C. Assuming an inductance value of one nanohenry, one can see that 6 nano-farads of capacitance would be required. Six nano-farads of capacitance is a relatively high value of capacitance. However, ceramic dielectrics that provide a very high dielectric constant are well known in the art and are very volumetrically efficient. They can also be made of biocompatible materials making them an ideal choice for use in the present invention.

Figure 13:
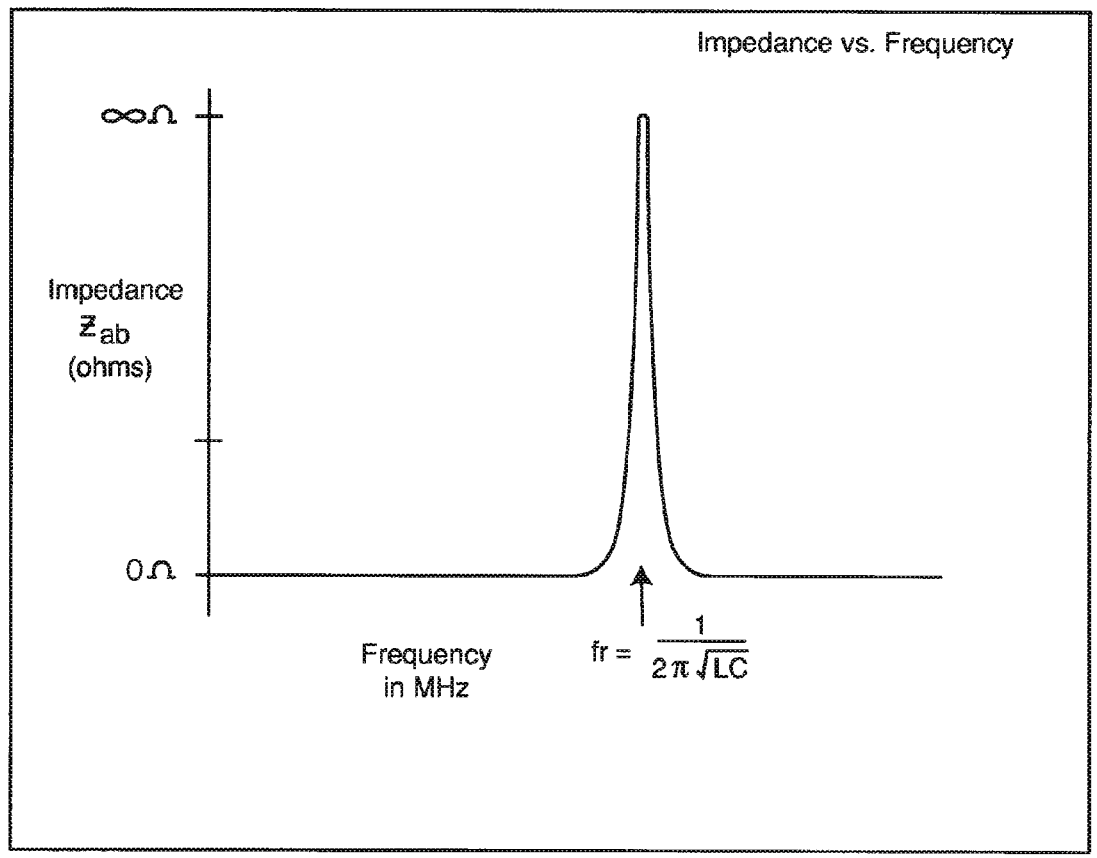
FIG. 13 is a graph showing impedance versus frequency for the parallel tank band stop circuit of FIG. 11.

FIG. 13 is a graph showing impedance versus frequency for the parallel tank, band stop filter circuit 146 of FIG. 11. As one can see, using ideal circuit components, the impedance measured between points A and B for the parallel tank circuit 146 shown in FIG. 11 is very low (zero) until one approaches the resonant frequency $f_r$. At the frequency of resonance, these ideal components combine together to look like a very high or, ideally, an infinite impedance. The reason for this comes from the denominator of the equation $Z_{ab}$ for the impedance for the inductor in parallel with the capacitor shown as FIG. 14. When the inductive reactance is equal to the capacitive reactance, the two imaginary vectors cancel each other and go to zero. Referring to the equations in FIGS. 14 and 15, one can see in the impedance equation for $Z_{ab}$, that a zero will appear in the denominator when $X_L=X_C$. This has the effect of making the impedance approach infinity as the denominator approaches zero. As a practical matter, one does not really achieve an infinite impedance. However, tests have shown that several hundred ohms can be realized which offers a great deal of attenuation and protection to RF pulsed currents from MRI. What this means is that at one particular unique frequency, the impedance between points A and B in FIG. 11 will appear very high (analogous to opening a switch). Accordingly, it would be possible, for example, in the case of a cardiac pacemaker, to design the cardiac pacemaker for compatibility with one single popular MRI system. For example, in the AIMD patient literature and physician manual it could be noted that the pacemaker lead wire system has been designed to be compatible with 3 Tesla MRI systems. Accordingly, with this particular device, a distal TIP band stop filter 146 would be incorporated where the L and the C values have been carefully selected to be resonant at 128 MHz, presenting a high or almost infinite impedance at the MRI pulse frequency.

Figure 16:
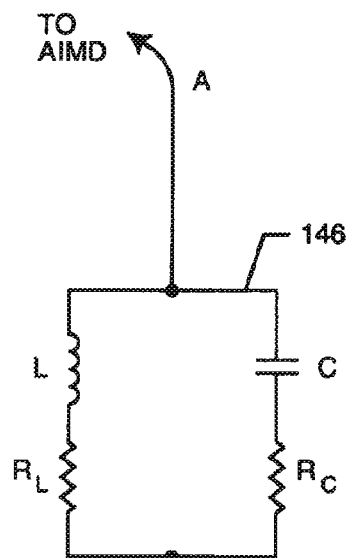
FIG. 16 is a schematic diagram illustrating the parallel tank circuit of FIG. 11, except in this case the inductor and the capacitor have series resistive losses.

FIG. 16 is a schematic drawing of the parallel tank circuit 146 of FIG. 11, except in this case the inductor L and the capacitor C are not ideal. That is, the capacitor C has its own internal resistance $R_C$, which is otherwise known in the industry as dissipation factor or equivalent series resistance (ESR). The inductor L also has a resistance $R_L$. For those that are experienced in passive components, one would realize that the inductor L would also have some parallel capacitance. This parasitic capacitance comes from the capacitance associated with adjacent turns. However, the inductance value contemplated is so low that one can assume that at MRI pulse frequencies, the inductor's parallel capacitance is negligible. One could also state that the capacitor C also has some internal inductance which would appear in series. However, the novel capacitors described below are very small or coaxial and have negligible series inductance. Accordingly, the circuit shown in FIG. 16 is a very good approximation model for the novel parallel tank circuits 146 as described herein.

This is best understood by looking at the FIG. 16 circuit 146 at the frequency extremes. At very low frequency, the inductor reactance equation is $X_L=2\pi fL$ (reference FIG. 15). When the frequency f is close to zero (DC), this means that the inductor looks like a short circuit. It is generally the case that biologic signals are low frequency, typically between 10 Hz and 1000 Hz. For example, in a cardiac pacemaker 100C, all of the frequencies of interest appear between 10 Hz and 1000 Hz. At these low frequencies, the inductive reactance $X_L$ will be very close to zero ohms. Over this range, on the other hand, the capacitive reactance $X_C$ which has the equation $X_C=1/(2\pi fc)$ will look like an infinite or open circuit (reference FIG. 15). As such, at low frequencies, the impedance between points A and B in FIG. 16 will equal to $R_L$. Accordingly, the resistance of the inductor ($R_L$) should, be kept as small as possible to minimize attenuation of biologic signals or attenuation of stimulation pulses to body tissues. This will allow biologic signals to pass through the band stop filter 146 freely. It also indicates that the amount of capacitive loss $R_C$ is not particularly important. As a matter of fact, it would be desirable if that loss were fairly high so as to not freely pass very high frequency signals (such as undesirable EMI from cellular phones). It is also desirable to have the Q of the circuit shown in FIG. 16 relatively low so that the band stop frequency bandwidth can be a little wider. In other words, in a preferred embodiment, it would be possible to have a band stop wide enough to block both 64 MHz and 128 MHz frequencies thereby making the medical device compatible for use in both 1.5 Tesla and 3 Tesla MRI systems.

Figure 17:
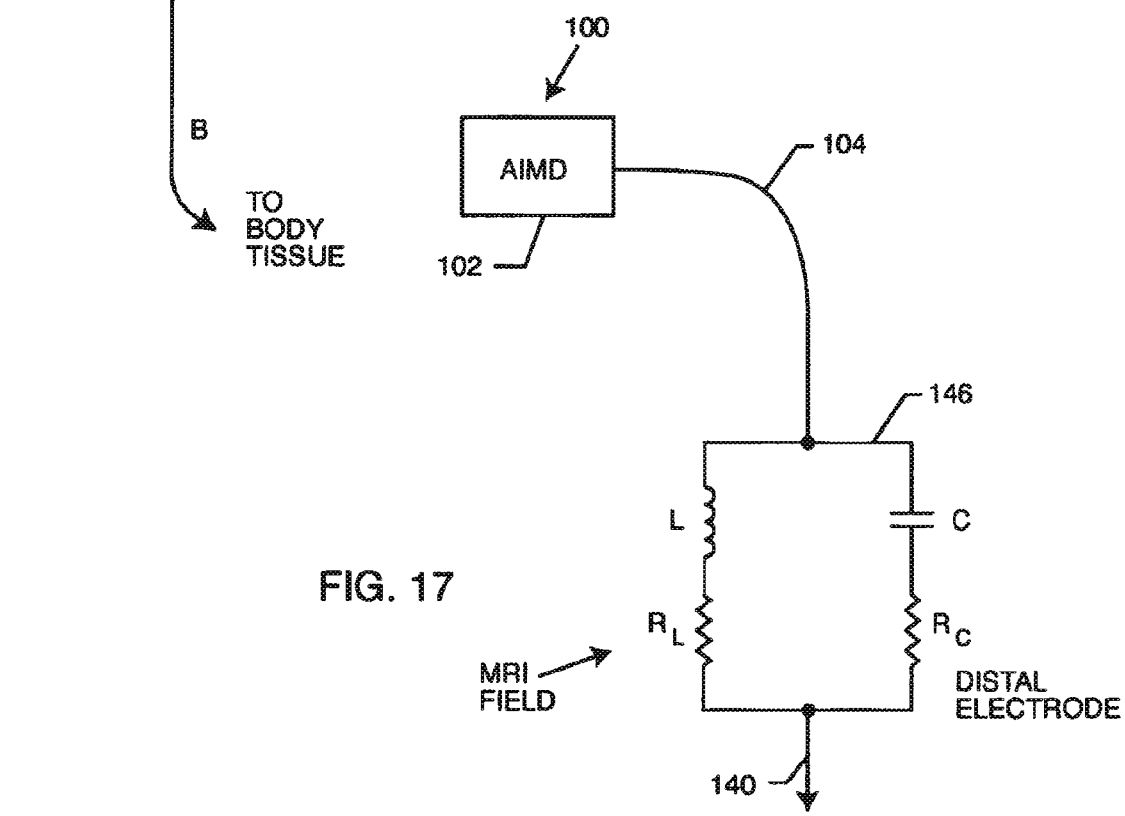
FIG. 17 is a diagram similar to FIG. 8, illustrating the tank circuit/band stop filter added near a distal electrode.

FIG. 17 is a drawing of the unipolar AIMD lead wire system, previously shown in FIG. 8, with the band stop filter 146 of the present invention added near the distal electrode 140. As previously described, the presence of the tank circuit 146 will present a very high impedance at one or more specific MRI RF pulse frequencies. This will prevent currents from circulating through the distal electrode 140 into body tissue at this selected frequency(s). This will provide a very high degree of important protection to the patient so that overheating does not cause tissue damage.

Figure 18:
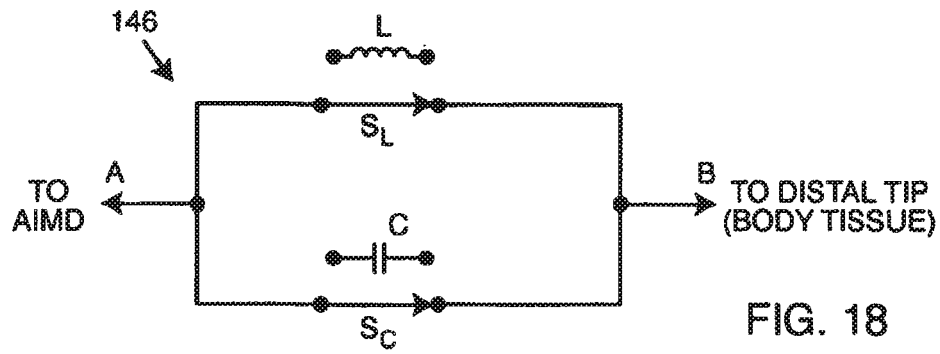
FIG. 18 is a schematic representation of the novel band stop tank filter of the present invention, using switches to illustrate its function at various frequencies.

FIG. 18 is a representation of the novel band stop tank filter 146 using switches that open and close at various frequencies to illustrate its function. Inductor L has been replaced with a switch $S_L$. When the impedance of the inductor is quite low, the switch $S_L$ will be closed. When the impedance or inductive reactance of the inductor is high, the switch $S_L$ will be shown open. There is a corresponding analogy for the capacitor element C. When the capacitive reactance looks like a very low impedance, the capacitor switch $S_C$ will be shown closed. When the capacitive reactance is shown as a very high impedance, the switch $S_C$ will be shown open. This analogy is best understood by referring to FIGS. 19, 20 and 21.

Figure 19:
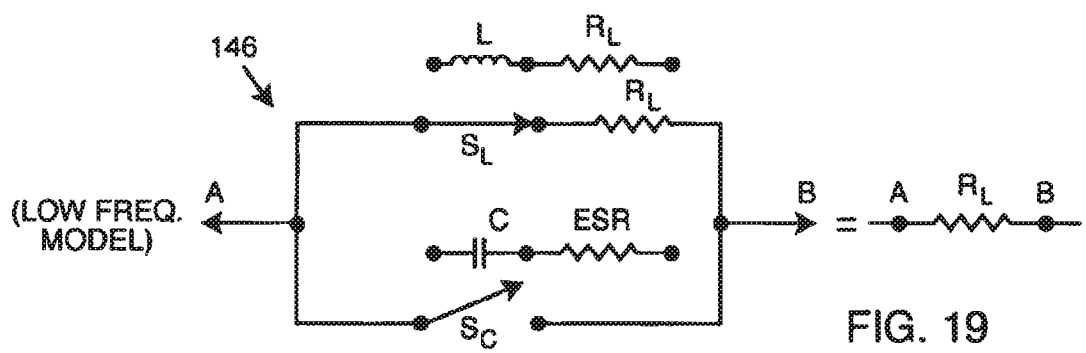
FIG. 19 is a schematic diagram similar to FIG. 18, illustrating the low frequency model of the band stop filter.

FIG. 19 is the low frequency model of the band stop filter 146. At low frequencies, capacitors tend to look like open circuits and inductors tend to look like short circuits. Accordingly, switch $S_L$ is closed and switch $S_C$ is open. This is an indication that at frequencies below the resonant frequency of the band stop filter 146 that currents will flow only through the inductor element and its corresponding resistance $R_L$. This is an important consideration for the present invention that low frequency biological signals not be attenuated. For example, in a cardiac pacemaker, frequencies of interest generally fall between 10 Hz and 1000 Hz. Pacemaker pacing pulses fall within this general frequency range. In addition, the implantable medical device is also sensing biological frequencies in the same frequency range. Accordingly, such signals must be able to flow readily through the band stop filter's inductor element. A great deal of attention should be paid to the inductor design so that it has a very high quality factor (Q) and a very low value of parasitic series resistance $R_L$.

Figure 20:
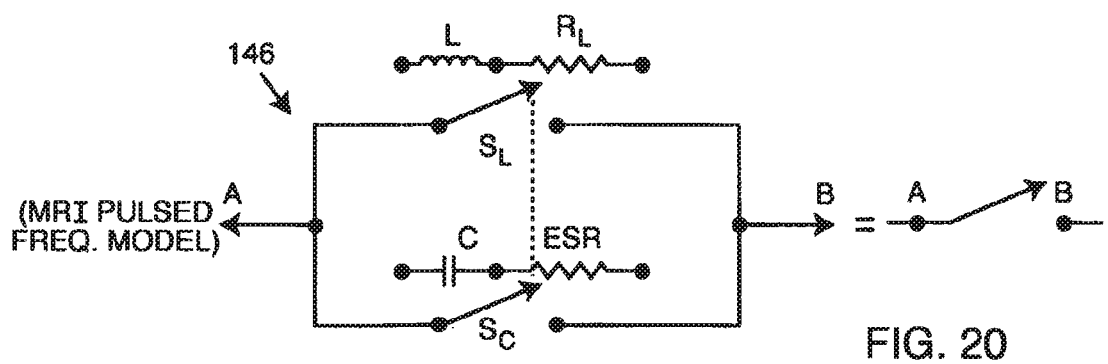
FIG. 20 is a schematic diagram similar to FIGS. 18 and 19, illustrating the model of the band stop filter of the present invention at its resonant frequency.

FIG. 20 is a model of the novel band stop filter 146 at its resonant frequency. By definition, when a parallel tank circuit is at resonance, it presents a very high impedance to the overall circuit. Accordingly, both switches $S_L$ and $S_C$ are shown open. For example, this is how the band stop filter 146 prevents the flow of MRI currents through pacemaker lead wires and/or into body tissue at a selected MRI RF pulsed frequency.

Figure 21:
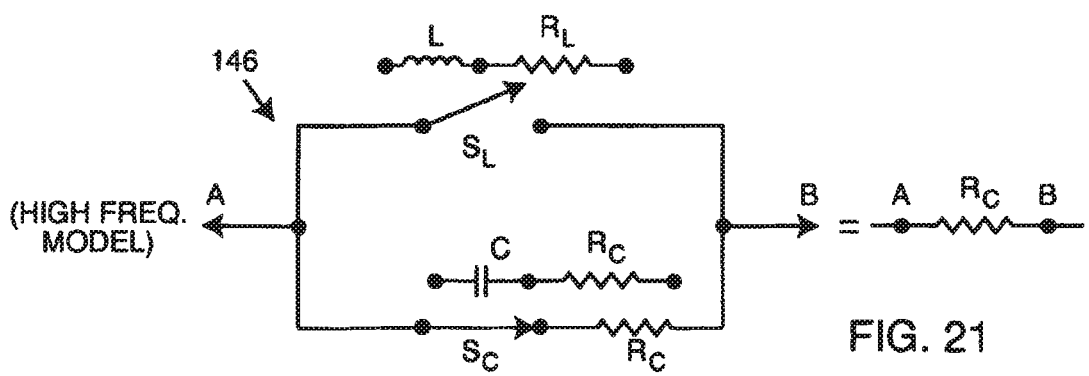
FIG. 21 is a schematic diagram similar to FIGS. 18-20, illustrating a model of the band stop filter at high frequencies well above the resonant frequency.

FIG. 21 is a model of the band stop filter 146 at high frequency. At high frequencies, inductors tend to look like open circuits. Accordingly, switch $S_L$ is shown open. At high frequencies, ideal capacitors tend to look like short circuits, hence switch $S_C$ is closed. It should be noted that real capacitors are not ideal and tend to degrade in performance at high frequency. This is due to the capacitor's equivalent series inductance and equivalent series resistance. Fortunately, for the present invention, it is not important how lossy (resistive) the capacitor element C gets at high frequency. This will only serve to attenuate unwanted electromagnetic interference from flowing in the lead wire system. Accordingly, in terms of biological signals, the equivalent series resistance $R_C$ and resulting quality factor of the capacitor element C is not nearly as important as the quality factor of the inductor element L. The equation for inductive reactance ($X_L$) is given in FIG. 15. The capacitor reactance equation ($X_C$) is also given in FIG. 15. As one can see, when one inserts zero or infinity for the frequency, one derives the fact that at very low frequencies inductors tend to look like short circuits and capacitors tend to look like open circuits. By inserting a very high frequency into the same equations, one can see that at very high frequency ideal inductors look like an infinite or open impedance and ideal capacitors look like a very low or short circuit impedance.

Figure 22:
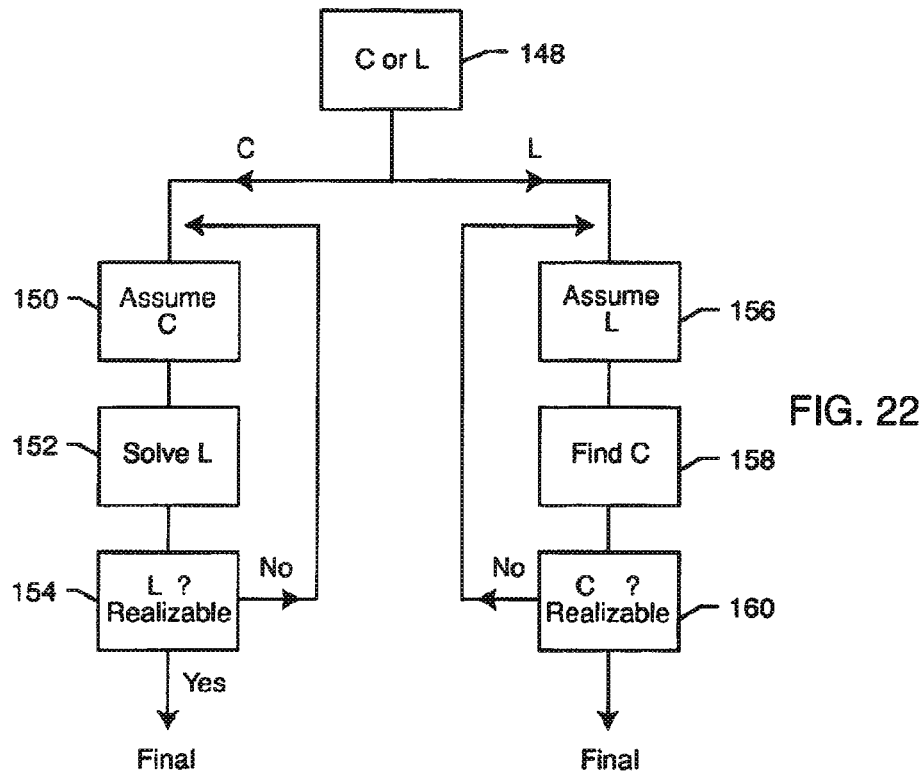
FIG. 22 is a decision tree block diagram illustrating a process for designing the band stop filters of the present invention.

FIG. 22 is a decision tree block diagram that better illustrates the design process herein. Block 148 is an initial decision step the designer must make. For illustrative purposes, we will start with a value of capacitance that is convenient. This value of capacitance is generally going to relate to the amount of space available in the AIMD lead wire system and other factors. These values for practical purposes generally range in capacitance value from a few tens of picofarads up to about 10,000 picofarads. This puts practical boundaries on the amount of capacitance that can be effectively packaged within the scope of the present invention. However, that is not intended to limit the general principles of the present invention, but just describe a preferred embodiment. Accordingly, in the preferred embodiment, one will select capacitance values generally ranging from 100 picofarads up to about 4000 picofarads and then solve for a corresponding inductance value required to be self-resonant at the selected telemetry frequency. Referring back to FIG. 22, one makes the decision whether the design was C first or L first. If one makes a decision to assume a capacitance value C first then one is directed to the left to block 150. In block 150, one does an assessment of the overall packaging requirements of a distal TIP 142 band stop filter 146 and then assumes a realizable capacitance value. So, in decision block 150, we assume a capacitor value. We then solve the resonant tank equation $f_r$ from FIG. 12 at block 152 for the required value of inductance (L). We then look at a number of inductor designs to see if the inductance value is realizable within the space, parasitic resistance $R_C$, and other constraints of the design. If the inductance value is realizable, then we go on to block 154 and finalize the design. If the inductance value is not realizable within the physical and practical constraints, then we need to go back to block 150 and assume a new value of capacitance. One may go around this loop a number of times until one finally comes up with a compatible capacitor and an inductor design. In some cases, one will not be able to achieve a final design using this alone. In other words, one may have to use a custom capacitor value or design in order to achieve a result that meets all of the design criteria. That is, a capacitor design with high enough internal losses $R_C$ and an inductor design with low internal loss $R_L$ such that the band stop filter 146 has the required quality factor (Q), that it be small enough in size, that it have sufficient current and high voltage handling capabilities and the like. In other words, one has to consider all of the design criteria in going through this decision tree.

In the case where one has gone through the left hand decision tree consisting of blocks 150, 152 and 154 a number of times and keeps coming up with a "no," then one has to assume a realizable value of inductance and go to the right hand decision tree starting at block 156. One then assumes a realizable value of inductance (L) with a low enough series resistance for the inductor $R_L$ such that it will work and fit into the design space and guidelines. After one assumes that value of inductance, one then goes to decision block 158 and solves the equation C in FIG. 12 for the required amount of capacitance. After one finds the desired amount of capacitance C, one then determines whether that custom value of capacitance will fit into the design parameters. If the capacitance value that is determined in step 160 is realizable, then one goes on and finalizes the design. However, if it is not realizable, then one can go back up to step 156, assume a different value of L and go through the decision tree again. This is done over and over until one finds combinations of L and C that are practical for the overall design.

For purposes of the present invention, it is possible to use series discrete inductors or parallel discrete capacitors to achieve the same overall result. For example, in the case of the inductor element L, it would be possible to use two, three or even more (n) individual inductor elements in series. The same is true for the capacitor element that appears in the parallel tank filter 146. By adding or subtracting capacitors in parallel, we are also able to adjust the total capacitance that ends up resonating in parallel with the inductance.

It is also possible to use a single inductive component that has significant parasitic capacitance between its adjacent turns. A careful designer using multiple turns could create enough parasitic capacitance such that the coil becomes self-resonant at a predetermined frequency. In this case, the pre-determined frequency would be the MRI pulsed frequency.

Figure 23:
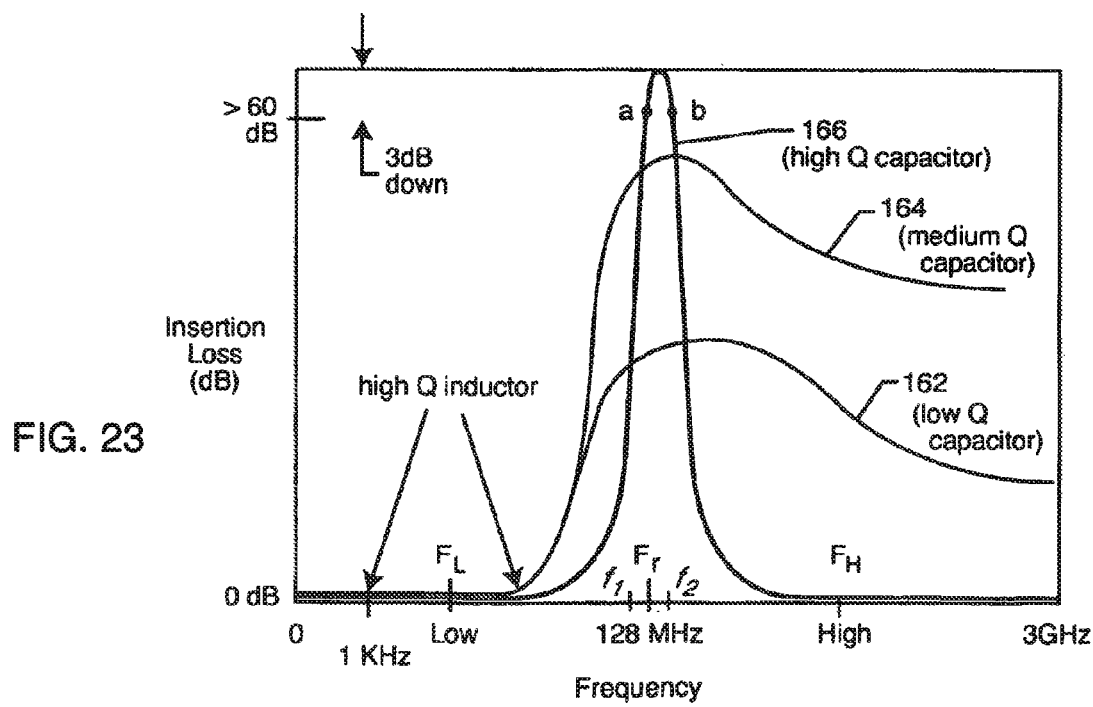
FIG. 23 is graph of insertion loss versus frequency for band stop filters having high Q inductors and differing quality "Q" factors.

Efficiency of the overall tank circuit 146 is also measured in terms of a quality factor, Q, although this factor is defined differently than the one previously mentioned for discrete capacitors and inductors. The circuit Q is typically expressed using the following equation:

$$Q = \frac{f_r}{\Delta f_{3dB}}$$

Where $f_r$ is the resonance frequency, and $\Delta f_{3dB}$ shown as points a and b in FIG. 23, is the bandwidth of the band stop filter 146. Bandwidth is typically taken as the difference between the two measured frequencies, $f_1$ and $f_2$, at the 3 dB loss points as measured on an insertion loss chart, and the resonance frequency is the average between $f_1$ and $f_2$. As can be seen in this relationship, higher Q values result in a narrower 3 dB bandwidth.

Material and application parameters must be taken into consideration when designing tank filters. Most capacitor dielectric materials age 1%-5% in capacitance values per decade of time elapsed, which can result in a shift of the resonance frequency of upwards of 2.5%. In a high-Q filter, this could result in a significant and detrimental drop in the band stop filter performance. A lower-Q filter would minimize the effects of resonance shift and would allow a wider frequency band through the filter. However, very low Q filters display lower than desirable attenuation behavior at the desired band stop frequency (see FIG. 23, curve 162). For this reason, the optimum Q for the band stop filter of the present invention will embody a high Q inductor L and a relatively low Q capacitor C which will result in a medium Q tank filter as shown in curve 164 of FIG. 23.

Accordingly, the "Q" or quality factor of the tank circuit is very important. As mentioned, it is desirable to have a very low loss circuit at low frequencies such that the biological signals not be undesirably attenuated. The quality factor not only determines the loss of the filter, but also affects its 3 dB bandwidth. If one does a plot of the filter response curve (Bode plot), the 3 dB bandwidth determines how sharply the filter will rise and fall. With reference to curve 166 of FIG. 23, for a tank that is resonant at 128 $MH_z$, an ideal response would be one that had infinite attenuation at 128 MHz, but had zero attenuation at low frequencies below 1 KHz. Obviously, this is not possible given the space limitations and the realities of the parasitic losses within components. In other words, it is not possible (other than at cryogenic temperatures) to build an inductor that has zero internal resistance. On the other hand, it is not possible to build a perfect (ideal) capacitor either. Capacitors have internal resistance known as equivalent series resistance and also have small amounts of inductance. Accordingly, the practical realization of a circuit, to accomplish the purposes of the present invention, is a challenging one.

The performance of the circuit is directly related to the efficiency of both the inductor and the capacitor; the less efficient each component is, the more heat loss that results, and this can be expressed by the addition of resistor elements to the ideal circuit diagram. The effect of lower Q in the tank circuit is to broaden the resonance peak about the resonance frequency. By deliberately using a low Q capacitor, one can broaden the resonance such that a high impedance (high attenuation) is presented at multiple MRI RF frequencies, for example 64 MHz and 128 $MH_z$.

Referring again to FIG. 23, one can see curve 164 wherein a low resistive loss high Q inductor has been used in combination with a relatively high ESR low Q capacitor. This has a very desirable effect in that at very low frequencies, the impedance of the tank circuit 146 is essentially zero ohms (or zero dB loss). This means that biologic frequencies are not undesirably attenuated. However, one can see that the 3 db bandwidth is much larger. This is desirable as it will block multiple RF frequencies. As one goes even higher in frequency, curve 164 will desirably attenuate other high frequency EMI signals, such as those from cellular telephones, microwave ovens and the like. Accordingly, it is often desirable that very low loss inductors be used in combination with relatively high loss (and/or high inductance) capacitors to achieve a medium or lower Q band stop filter. Again referring to FIG. 23, one can see that if the Q of the overall circuit or of the individual components becomes too low, then we have a serious degradation in the overall attenuation of the band stop filter at the MRI pulse frequencies. Accordingly, a careful balance between component design and tank circuit Q must be achieved.

Referring once again to FIG. 17, one can also increase the value of $R_C$ by adding a separate discrete component in series with the capacitor element. For example, one could install a small capacitor chip that had a very low equivalent series resistance and place it in series with a resistor chip. This would be done to deliberately raise the value of $R_C$ in the circuit as shown in FIG. 17. By carefully adjusting this value of $R_C$, one could then achieve the ideal curve 164 as shown in FIG. 23.

Figure 24:
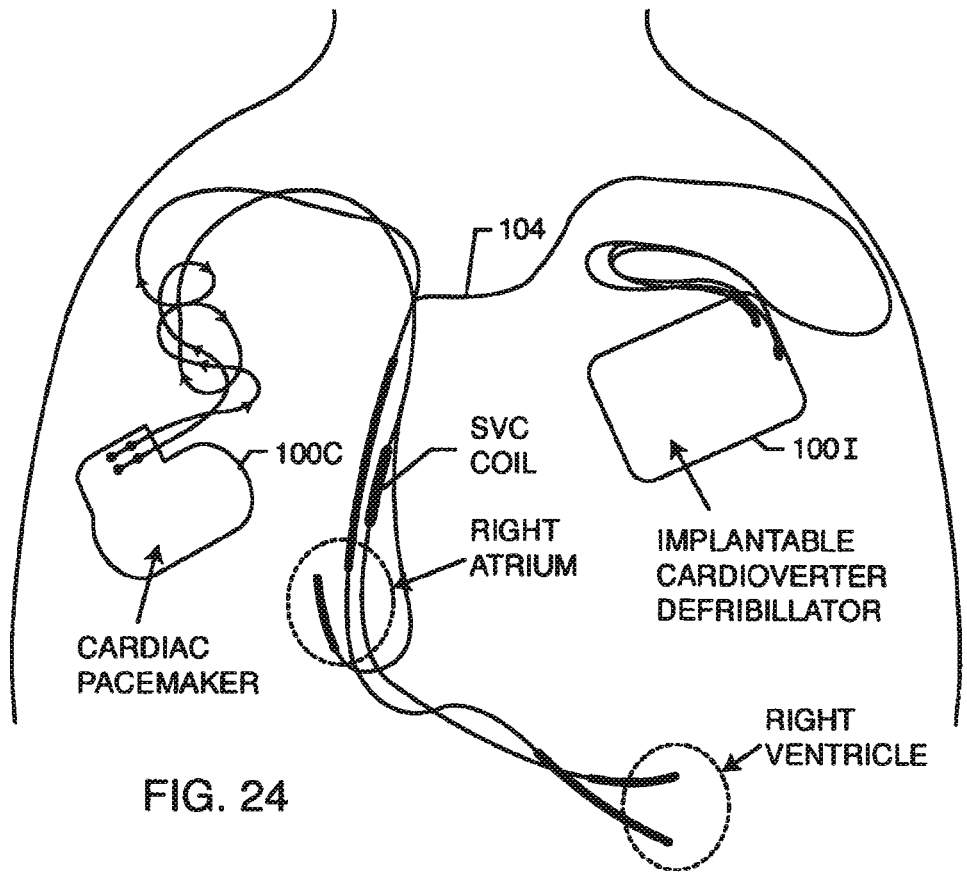
FIG. 24 is a tracing of an exemplary patient x-ray showing an implanted pacemaker and cardioverter defibrillator and corresponding lead wire system.

FIG. 24 is a tracing of an actual patient X-ray. This particular patient required both a cardiac pacemaker 100C and an implantable cardioverter defibrillator 100I. The corresponding lead wire system 104, as one can see, makes for a very complicated antenna and loop coupling situation. The reader is referred to the article entitled, "Estimation of Effective Lead Loop Area for Implantable Pulse Generator and Implantable Cardioverter Defibrillators" provided by the AAMI Pacemaker EMC Task Force.

Referring again to FIG. 24, one can see that from the pacemaker 100C, there is an electrode in both the right atrium and in the right ventricle. Both these involve a TIP and RING electrode. In the industry, this is known as a dual chamber bipolar lead wire system. Accordingly, the band stop filters 146 of the present invention would need to be placed at least in the distal TIP in the right atrium and the distal TIP in the right ventricle from the cardiac pacemaker. One can also see that the implantable cardioverter defibrillator (ICD) 100I is implanted directly into the right ventricle. Its shocking TIP and perhaps its super vena cava (SVC) shock coil would also require a band stop filters of the present invention so that MRI exposure cannot induce excessive currents into the associated lead wire system (S). Modern implantable cardioverter defibrillators (ICDs) incorporate both pacing and cardioverting (shock) features. Accordingly, it is becoming quite rare for a patient to have a lead wire layout as shown in the X-ray of FIG. 24. However, the number of electrodes remain the same. There are also newer combined pacemaker/ICD systems which include biventricular pacemaking (pacing of the left ventricle). These systems can have as many as 9 to even 12 lead wires.

Figure 25:
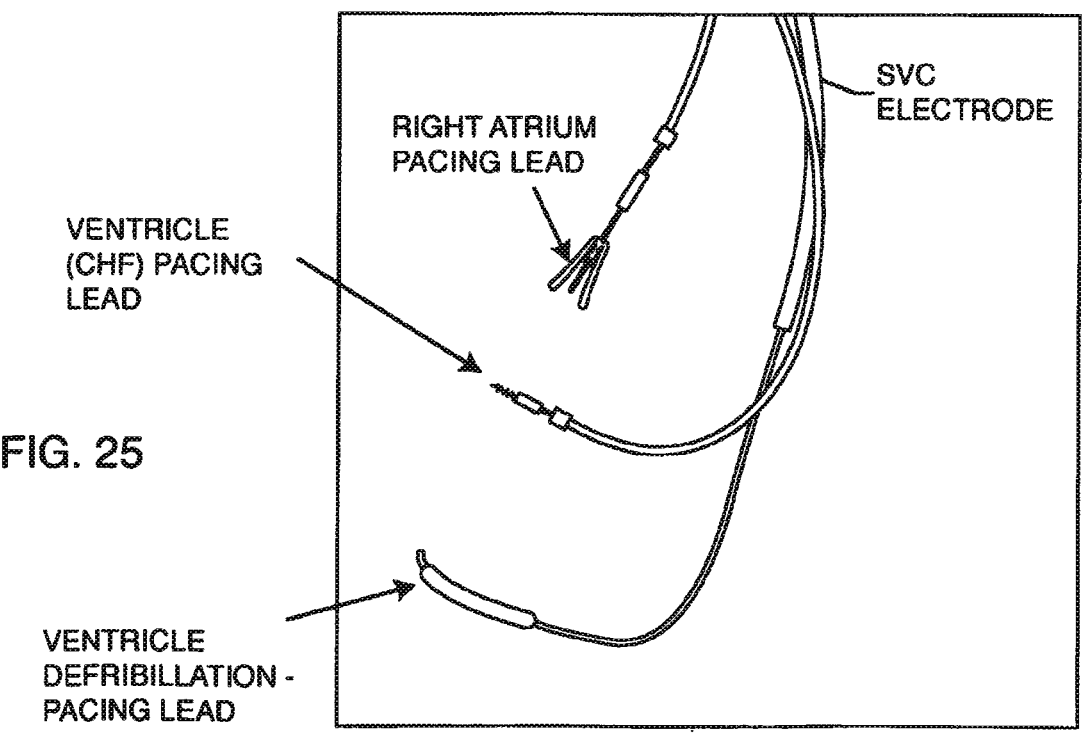
FIG. 25 is a line drawings of an exemplary patent cardiac x-ray of a bi-ventricular lead wire system.

FIG. 25 is a line drawing of an actual patient cardiac X-ray of one of the newer bi-ventricular lead wire systems with various types of electrode TIPS shown. The new bi-ventricular systems are being used to treat congestive heart failure, and make it possible to implant leads outside of the left ventricle. This makes for a very efficient pacing system; however, the lead wire system 104 is quite complex. When a lead wire system 104, such as those described in FIGS. 8, 9, 10 and 11, are exposed to a time varying electromagnetic field, electric currents can be induced into such lead wire systems. For the bi-ventricular system, band stop filters 146 would be required at each of the three distal TIPs and optionally at RING and SVC locations.

Figure 26:
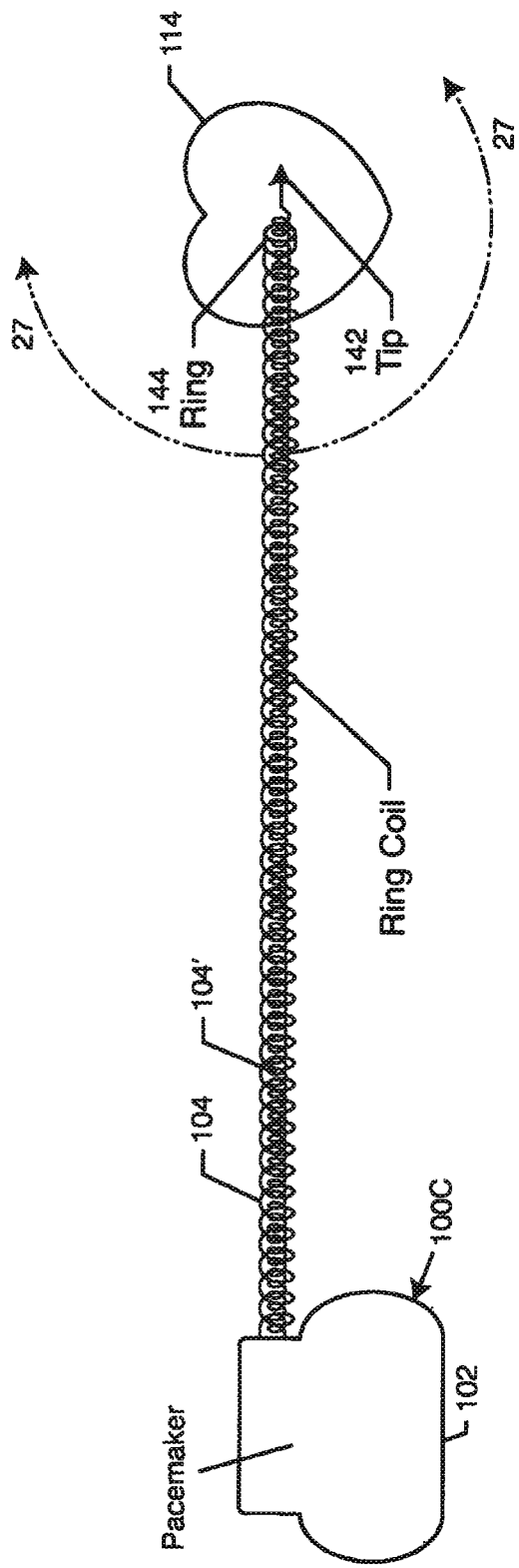
FIG. 26 illustrates a bipolar cardiac pacemaker lead wire showing the distal TIP and the distal RING electrodes.

FIG. 26 illustrates a single chamber bipolar cardiac pacemaker lead wire showing the distal TIP 142 and the distal RING 144 electrodes. This is a spiral wound system where the RING coil 104 is wrapped around the TIP coil 104'. There are other types of pacemaker lead wire systems in which these two leads lay parallel to one another (known as a bifilar lead system).

Figure 27:
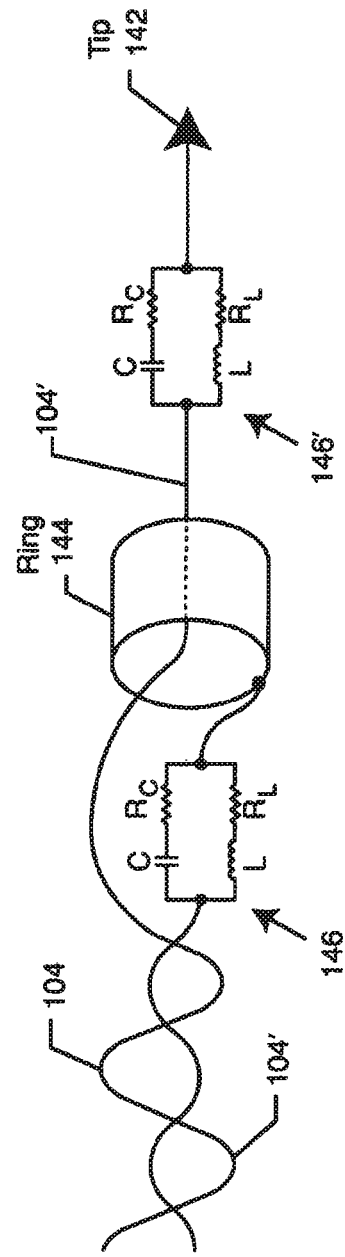
FIG. 27 is an enlarged, fragmented schematic illustration of the area illustrated by the line 27-27 in FIG. 26.

FIG. 27 is a schematic illustration of the area 27-27 in FIG. 26. In the area of the distal TIP 142 and RING 144 electrodes, band stop filters 146 and 146' have been placed in series with each of the respective TIP and RING circuits. Accordingly, at MRI pulsed frequencies, an open circuit will be presented thereby stopping the flow of undesirable RF current.

Although several embodiments of the invention have been described in detail, for purposes of illustration, various modifications of each may be made without departing from the spirit and scope of the invention. Accordingly, the invention is not to be limited, except as by the appended claims.

What is claimed is:
1. An implantable medical lead, comprising:
a) an implantable lead wire;
b) an electrode that is adapted to be placed in contact with biological cells; and
c) a coil comprising multiple turns of conductive material, wherein the coil is in series with the lead wire and the electrode, d) wherein an inductance and a capacitance of the coil result in the coil having a self-resonance at a resonant frequency, and e) wherein the inductance and an inductor resistance provide a relatively low impedance from 10 Hz to 1 kHz such that the coil permits passage of biological signals having frequencies from 10 Hz to 1 kHz, and f) wherein a capacitance reactance and a capacitance resistance substantially act as an open circuit to the same biological signals having the frequencies from 10 Hz to 1 kHz that the inductance and inductor resistance permit to pass, and g) wherein the coil has relatively high impedance at the resonant frequency, and h) wherein the self-resonance has a Q having a 3 dB bandwidth that is on the order of MHz.

2. The implantable medical lead of claim 1 wherein the resonant frequency of the coil is an MRI pulsed frequency.

3. The implantable medical lead of claim 1 wherein the resonant frequency of the coil is one of 64 MHz and 128 MHz.

4. The implantable medical lead of claim 1 wherein the coil blocks all frequencies in a band about the resonant frequency.

5. The implantable medical lead of claim 1 wherein the resonant frequency of the coil is on the order of tens of megahertz.

6. The implantable medical lead of claim 1 wherein the coil is near the electrode.

7. The implantable medical lead of claim 1 wherein the coil is integrated with the electrode.

8. The implantable medical lead of claim 1 as a bipolar or bifilar lead wire system comprising the implantable lead wire, wherein the electrode comprises one of a RING electrode and a TIP electrode.

9. The implantable medical lead of claim 1 as a bipolar or bifilar lead wire system comprising the implantable lead wire, wherein the electrode comprises one of a RING electrode and a TIP electrode, and wherein the coil is integrated with the electrode.

10. The implantable medical lead of claim 1 further comprising a second coil in series with the lead wire and the electrode.

11. The implantable medical lead of claim 1 wherein the electrode comprises a RING electrode, and the coil is integrated with the RING electrode.

12. The implantable medical lead of claim 1 wherein the electrode comprises a TIP electrode, and the coil is integrated with the TIP electrode.

13. The implantable medical lead of claim 1 wherein the coil is an air wound coil.

14. The implantable medical lead of claim 1 wherein the resonant frequency of the coil is not affected by MRI signals or fields.

15. An implantable medical lead, comprising:
a) an implantable lead wire comprising a conductor;
b) an electrode, wherein the electrode is contactable to biological cells; and
c) a coil comprising multiple turns of conductive material, wherein the coil is self-resonant at a resonant frequency;
d) wherein the conductor, the electrode, and the coil are conductively connected in series with one another;
e) wherein the coil has a relatively low impedance from 10 Hz to 1 kHz such that the coil permits passage of biological signals having frequencies from 10 Hz to 1 kHz; and
f) wherein the resonant frequency is above 1 kHz and the coil has a relatively high impedance at the resonant frequency.

16. The implantable medical lead of claim 15 wherein the resonant frequency is on the order of MHz.

17. The implantable medical lead of claim 15 wherein the resonant frequency is on the order of tens of MHz.

18. The implantable medical lead of claim 15 wherein the resonant frequency is an MRI pulsed frequency.

19. The implantable medical lead of claim 15 wherein the resonant frequency is one of 64 MHz and 128 MHz.

20. An implantable medical lead, comprising:
a) a lead wire having a length extending from a proximal lead wire end to a distal lead wire portion;
b) an electrode electrically connected to the distal lead wire portion, wherein the electrode is adapted to be placed in contact with biological cells; and
c) a band stop filter consisting of at least one inductive component having multiple turns of a conductive material and being disposed somewhere along the length of the lead wire in series with the electrode,
d) wherein the band stop filter has a relatively low inductance and an inductor resistance such that at low frequencies from 10 Hz to 1 kHz the band stop filter permits passage of biological signals frequencies from 10 Hz to 1 kHz, and
e) wherein the band stop filter has parasitic capacitance between the multiple turns of the conductive material of the at least one inductive component such that at the low frequencies from 10 Hz to 1 kHz, a capacitance reactance and a capacitance resistance substantially act as an open circuit to the same biological signals that the inductance and inductor resistance permit to pass, and
f) wherein the band stop filter has a relatively high impedance at a resonant frequency with a Q at the resonant frequency having a 3 dB bandwidth that is on the order of MHz.

21. The implantable lead of claim 20 wherein the resonant frequency is one of 64 MHz and 128 MHZ.

22. The implantable lead of claim 20 wherein the electrode is selected from a TIP electrode and a RING electrode.

23. An implantable medical lead, comprising:
a) an implantable lead wire having a length extending from a proximal lead wire end to a distal lead wire portion, wherein the proximal lead wire end is connectable to a pulse generator;
b) an electrode electrically connected to the distal lead wire portion, wherein the electrode is adapted to be placed in contact with biological cells; and
c) a coil comprising multiple turns of conductive material, wherein the coil, the electrode, and the lead wire are in series with one another;
d) wherein an inductance and a capacitance of the coil result in the coil having a self-resonance at a resonant frequency, and
e) wherein the inductance and an inductor resistance provide a relatively low impedance from 10 Hz to 1 kHz such that the coil permits passage of biological signals having frequencies from 10 Hz and 1 kHz, and
f) wherein a capacitance reactance and a capacitance resistance substantially act as an open circuit to the same biological signals having the frequencies from 10 Hz to 1 kHz that the inductance and inductor resistance permit to pass, and
g) wherein the coil has a relatively high impedance that blocks signals at the resonant frequency.

* * * * *

UNITED STATES PATENT AND TRADEMARK OFFICE
CERTIFICATE OF CORRECTION

| | | |
|---|---|---|
| PATENT NO. | : 9,248,283 B2 | |
| APPLICATION NO. | : 14/080830 | |
| DATED | : February 2, 2016 | |
| INVENTOR(S) | : Henry R. Halperin and Robert A. Stevenson | |

It is certified that error appears in the above-identified patent and that said Letters Patent is hereby corrected as shown below:

On the title page,

Page 4, Column 2, 4th reference in U.S. PATENT DOCUMENTS, delete "Vohl" and insert --Viohl--

Page 4, Column 2, 5th reference in U.S. PATENT DOCUMENTS, delete "Vohl" and insert --Viohl--

Page 5, Column 1, (56) References Cited OTHER PUBLICATIONS, line 1 of 4th reference, delete "Constatine" and insert --Constantine--

Page 5, Column 2, (56) References Cited OTHER PUBLICATIONS, line 2 of 2nd reference, delete "Provisonal" and insert --Provisional--

Page 5, Column 2, (56) References Cited OTHER PUBLICATIONS, line 4 of 5th reference, delete "INternational" and insert --International--

Page 5, Column 2, (56) References Cited OTHER PUBLICATIONS, line 1 of 6th reference, delete "Mr" and insert --MR--

In the drawings,

Sheet 11 of 12, Figure 24 item 100I delete "DEFRIBILLATOR" and insert --DEFIBRILLATOR--

Sheet 11 of 12, Figure 25, at the left side of the figure in the lower phrase description beneath the words "FIG. 25" delete "DEFRIBILLATION" and insert --DEFIBRILLATION--

In the specification,

Column 6, line 36 delete "effect" and insert --affect--

Signed and Sealed this
Nineteenth Day of July, 2016

Michelle K. Lee
*Director of the United States Patent and Trademark Office*

Column 11, line 27 delete "blopolar" and insert --bipolar--

Column 12, line 47 delete "knows" and insert --known--